United States Patent
Kerovuo et al.

(10) Patent No.: US 9,677,053 B2
(45) Date of Patent: Jun. 13, 2017

(54) LACCASES FOR BIO-BLEACHING

(71) Applicants: BASF ENZYMES LLC, San Diego, CA (US); BASF SE, Ludwigshafen am Rhein (DE)

(72) Inventors: Janne Samuli Kerovuo, San Diego, CA (US); Sylke Haremza, Neckargemuend (DE); Oliver Koch, Eppelheim (DE); Tilo Habicher, Speyer (DE); Dan E. Robertson, Belmont, MA (US); Grace Desantis, San Diego, CA (US); Ryan McCann, San Diego, CA (US); Peter Luginbuhl, San Diego, CA (US)

(73) Assignees: BASF Enzymes LLC, San Diego, CA (US); BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/141,467

(22) Filed: Apr. 28, 2016

(65) Prior Publication Data

US 2016/0237411 A1    Aug. 18, 2016

Related U.S. Application Data

(62) Division of application No. 14/591,449, filed on Jan. 7, 2015, now Pat. No. 9,353,477, which is a division of application No. 13/745,394, filed on Jan. 18, 2013, now Pat. No. 8,951,766, which is a division of application No. 12/439,459, filed as application No. PCT/US2007/019124 on Aug. 31, 2007, now Pat. No. 8,377,670.

(60) Provisional application No. 60/824,402, filed on Sep. 1, 2006.

(51) Int. Cl.

| | | |
|---|---|---|
| C12N 9/02 | (2006.01) |
| C12N 15/00 | (2006.01) |
| C12P 21/06 | (2006.01) |
| C12P 21/04 | (2006.01) |
| C07H 21/04 | (2006.01) |
| C12N 15/09 | (2006.01) |
| C12P 5/00 | (2006.01) |
| C12P 7/00 | (2006.01) |
| C12P 19/00 | (2006.01) |
| D21C 9/10 | (2006.01) |
| D21C 9/00 | (2006.01) |
| D21C 5/00 | (2006.01) |

(52) U.S. Cl.
CPC .......... *C12N 9/0061* (2013.01); *C12N 15/09* (2013.01); *C12P 5/00* (2013.01); *C12P 7/00* (2013.01); *C12P 19/00* (2013.01); *D21C 9/005* (2013.01); *D21C 9/1063* (2013.01); *C12Y 110/03002* (2013.01); *D21C 5/005* (2013.01)

(58) Field of Classification Search
CPC .................................................. C12N 9/0061
See application file for complete search history.

(56) References Cited

U.S. PATENT DOCUMENTS

| | | |
|---|---|---|
| 5,667,531 A | 9/1997 | Yaver |
| 5,770,418 A | 6/1998 | Yaver |
| 5,795,760 A | 8/1998 | Berka |
| 5,981,243 A | 11/1999 | Berka |
| 6,015,783 A | 1/2000 | Von Der Osten |
| 6,200,786 B1 | 3/2001 | Huang |
| 2005/0089980 A1 | 4/2005 | Kruus |

FOREIGN PATENT DOCUMENTS

| | | |
|---|---|---|
| EP | 1083233 | 3/2001 |
| EP | 1167528 | 1/2002 |
| EP | 1300469 | 4/2003 |
| WO | WO97/28243 | 8/1997 |
| WO | WO01/92498 | 12/2001 |
| WO | 02/42444 A2 | 5/2002 |
| WO | 2005021714 A2 | 3/2005 |
| WO | WO2006/032724 | 3/2006 |

OTHER PUBLICATIONS

Berka—Appl. Envir. Microbiol. (1997)—63—3151-3157.
Borriss—Microbiology (1996)—142—3027-3031.
Bourbonnais—Appl. Envir. Microbiol. (1995)—61—1876-1880.
Broun—Science (1998)—282—1315-1317.
EP04801982—EP Search Report—Jul. 7, 2008.
Fabbrini—J. Mol. Catalysis B: Enzymatic (2002)—16—231-240.
GenBank Accession No. AB007638 (1999)—Bacillus subtilis.
Guo—Proceedings of the National Academy of Science (2004)—101—9205-9210.
Kasahara—DNA Research (1997)—4—335-339.
Leonowicz—Journal of Basic Microbiology (2001)—3-4—185-227.
NCBI Accession No. Q1DNW1—Birren (2006)—1-3.
PCT/US2004/25932—ISR & WO—Sep. 13, 2006.
PCT/US2007/19124—ISR & WO—Jun. 12, 2008.
Piontek—Journal of Biological Chemistry (2002)—277—37663-37669.
Seffernick—Journal of Bacteriology (2001)—183—2405-2410.
PCT/US2004/25932—ISR & WO—Sequence Search Results—Sep. 13, 2006.
Slomczynski—Applied and Environmental Microbiology (1995)—61—907-912.
Swiss-Prot Accession No. P07788 (1988) Cota Bacsu.
Ten Have—Chem. Rev (2001)—101—3397-3414.
Van De Welde—Journal of Molecular Catalysis B: Enzymatic (1999)—6—453-461.
Witkowski—Biochemistry (1999)—38—11643-11650.

(Continued)

*Primary Examiner* — Yong Pak
(74) *Attorney, Agent, or Firm* — Richa Dhindsa

(57) ABSTRACT

Provided herein are isolated laccase enzymes and nucleic acids encoding them. Also provided are mediators for laccase reactions. Also provided herein are methods for using laccases to oxidize lignins, other phenolic, and aromatic compounds, such as for bio-bleaching and decolorization of wood pulp under high temperature and pH conditions to facilitate a substantial reduction in use of bleaching chemicals, as well as for treatment of fibers.

5 Claims, 6 Drawing Sheets

(56) References Cited

OTHER PUBLICATIONS

EP07837576—Supplementary EP Search Report—Nov. 16, 2009.
Baldrian—FEMS Microbiology Reviews (2006)—30—215-242.
Hernandez—Appl. Microbiol. Biotechnol. (2006)—70—212-221.
Machczynski—Protein Science (2004)—13—2388-2397.
Nakamura—CMLS Cell. Mol. Life Sci. (2005)—62—2050-2066.
Ruijssenaars—Appl Microbiol Biotechnol (2004)—65—177-182.
Sulistyaningdyah—FEMS Microbiology Letters (2004)—230—209-214.
Branden—Introduction to Protein Structure, Garland Publishing Inc., New York, p. 247 (1991).
EPO—Nov. 15, 2012—94(3) Communication—EP 11194671.1.
SIPO—Feb. 16, 2013—First Office Action & Translation—CN201110378647.4.
USPTO—Jun, 28, 2012—Office Action and Form 892—U.S. Appl. No. 12/439,459.
USPTO—May 22, 2014—Office Action, Form 892, IDSs Considered—U.S. Appl. No. 13/754,394.
EP11194671.1—Extended EP Search Report and Opinion—Feb. 14, 2012.
EP11194671.1—Article 94(3) Communication—Nov. 15, 2012.
EP 07837576—Article 94(3) Communication—Feb. 3, 2011.
EP 04801982.2—Article 94(3) Communication—Mar. 14, 2011.
CIPO—Jul. 14, 2011—Office Action—CA2535526.
SIPO—Aug. 8, 2011—Decision of Rejection—CN200780040619.3.

SEQUENCE LISTING

<160> NUMBER OF SEQ ID NOS: 4

<210> SEQ ID NO 1

-continued

```
<211> LENGTH: 2105
<212> TYPE: DNA
<213> ORGANISM: Cochliobolus hetersotrophus

<400> SEQUENCE: 1
atggtctctt caatttcgag ggtggttacc gcccttgggc ttcttttgcc cactgtcact      60
tcatctgttg tacctcataa aagtctcgcc cccagaacac cggaggttcc ttggaagaac     120
actggtctct tcagtggaca cagcaaacga caaggatatg agactgcctg taatcatggt     180
ccagaatcaa gaggatgctg gattgacgac ttcaacatcg acaccgacat ggatgttgaa     240
tggccagata ctggaaagac agtcaagtat cacctgacca tcaccaatac cactggagct     300
ccagacggtt ttgaaaggcc gatgttcttg attaatggcc aatacccagg accagtaagt     360
gctgtgttaa aatgccaata attcttttct aatgagtcat agactattac tgccgactgg     420
ggagatgttc tagagatcac agttaccaat ggccttgaaa acaacggtac aggtatacat     480
tggcacggtc tgaggcaact cgggacaaac gaacaagatg gcgtaaatgg tatcactgaa     540
tgcccaatcg cacccggtga ctccaagctc tacagattca aagcaactca atatggcact     600
accgtaagta tcacacactg tgtgtgtatg acatgtttcc ggaagacggc taaccgctac     660
agtggtatca ctcgcactac tcggtgcagt atggtgacgg catcgtgggt cctctgatca     720
tcaaaggacc ctcaacggcg aactacgata ttgatcttgg cgctttccca atgactgact     780
ggtttcacgc aaccaccttc accgtcaacg ctgcagccgt tcatgcaaat ggccctccaa     840
ctgctgacaa tgtccttgtc aatggctcca tgacctcatc ttttggcggc aagtacgccg     900
aaacgatcct aactccggga aaatctcact tgctgcgttt gatgaacgtt ggtattaaca     960
actaccttca tgtcggcctc gatgggcatc agttccaggt catttcggct gatttcacgc    1020
ccattgaacc tttctacacg gacagcttgg tccttgcagt cggtaagttg aaccgaagtt    1080
gtgtccagat gcaagcccgt tttgtttatc acaacatcgt tctgtgtgac gacaccccgg    1140
ccacgagaat gtagtcgaaa tagccactgt tgatgaacgt ttcactaaca acgtcgccag    1200
gtcaacggta tgaagtcatc atcaacgcaa ctgaagctgt gggcaactac tggctacgtg    1260
ttggtaccgg cggtaactgc gacggtccca atgccaatgc agcaaatatc aggagtatct    1320
tccgatatgc tggcgctcca actgaagacc cagacacgac tggttcgctt ccgtcgggct    1380
gctacgatga ggatgttgta ccctatgcca agacgactgt tcctcaggag atgcccgaac    1440
agttgagcgt gggcttcaac cctaactgga ctagtgacgt gacgcaaaat cagggtctgg    1500
tccaatggct cgtcaacggt aatcccatgg cagttgatct tgaagtccct actctgcagt    1560
cggtgttgga tggcaatgtt acctacggaa acaaccgcca cgtgtttgca gtcgacgaga    1620
aacaccaagt aagtcgtccc ctgtacttag tactgtttaa tggtcattaa caaaggcttc    1680
agtggcaata ttgggtcatc caacaaaaca gttctaaccc accacttcct caccccatcc    1740
acctccacgg ccacgacttc tacgtcctcg cacaggtcga aaacgcagtc tggaacggag    1800
atatttcaac cctgaagacg gacaacccca tccgtcggga cacggccgat cttcccgctg    1860
gaggctactt ggtccttgct ttcgagtcgg acaaccctgg cgcatggctt atgcactgcc    1920
acatcccctt ccacgttgct gccggtctcg gtgtccagtt cctcgagcgc gaatccgaaa    1980
tcaaggccca agatggatac gcagagatgc acaggacatg tgctaactgg cagtcatggc    2040
gctacaagta ccatcccaat ggcatcttgt tccccggtga ctctggtcta cgtcgtcgca    2100
actaa                                                                2105
```

```
<210> SEQ ID NO 2
<211> LENGTH: 601
<212> TYPE: PRT
<213> ORGANISM: Cochliobolus heterostrophus

<400> SEQUENCE: 2

Met Val Ser Ser Ile Ser Arg Val Val Thr Ala Leu Gly Leu Leu
 1               5                   10                  15

Pro Thr Val Thr Ser Ser Val Val Pro His Lys Ser Leu Ala Pro Arg
                20                  25                  30

Thr Pro Glu Val Pro Trp Lys Asn Thr Gly Leu Phe Ser Gly His Ser
            35                  40                  45

Lys Arg Gln Gly Tyr Glu Thr Ala Cys Asn His Gly Pro Glu Ser Arg
        50                  55                  60

Gly Cys Trp Ile Asp Asp Phe Asn Ile Asp Thr Asp Met Asp Val Glu
 65                  70                  75                  80

Trp Pro Asp Thr Gly Lys Thr Val Lys Tyr His Leu Thr Ile Thr Asn
                85                  90                  95

Thr Thr Gly Ala Pro Asp Gly Phe Glu Arg Pro Met Phe Leu Ile Asn
            100                 105                 110

Gly Gln Tyr Pro Gly Pro Thr Ile Thr Ala Asp Trp Gly Asp Val Leu
        115                 120                 125

Glu Ile Thr Val Thr Asn Gly Leu Glu Asn Asn Gly Thr Gly Ile His
130                 135                 140

Trp His Gly Leu Arg Gln Leu Gly Thr Asn Glu Gln Asp Gly Val Asn
145                 150                 155                 160

Gly Ile Thr Glu Cys Pro Ile Ala Pro Gly Asp Ser Lys Leu Tyr Arg
                165                 170                 175

Phe Lys Ala Thr Gln Tyr Gly Thr Thr Trp Tyr His Ser His Tyr Ser
            180                 185                 190

Val Gln Tyr Gly Asp Gly Ile Val Gly Pro Leu Ile Ile Lys Gly Pro
        195                 200                 205

Ser Thr Ala Asn Tyr Asp Ile Asp Leu Gly Ala Phe Pro Met Thr Asp
    210                 215                 220

Trp Phe His Ala Thr Thr Phe Thr Val Asn Ala Ala Val His Ala
225                 230                 235                 240

Asn Gly Pro Pro Thr Ala Asp Asn Val Leu Val Asn Gly Ser Met Thr
                245                 250                 255

Ser Ser Phe Gly Gly Lys Tyr Ala Glu Thr Ile Leu Thr Pro Gly Lys
            260                 265                 270

Ser His Leu Leu Arg Leu Met Asn Val Gly Ile Asn Asn Tyr Leu His
        275                 280                 285

Val Gly Leu Asp Gly His Gln Phe Gln Val Ile Ser Ala Asp Phe Thr
    290                 295                 300

Pro Ile Glu Pro Phe Tyr Thr Asp Ser Leu Val Leu Ala Val Gly Gln
305                 310                 315                 320

Arg Tyr Glu Val Ile Ile Asn Ala Thr Glu Ala Val Gly Asn Tyr Trp
                325                 330                 335

Leu Arg Val Gly Thr Gly Gly Asn Cys Asp Gly Pro Asn Ala Asn Ala
            340                 345                 350

Ala Asn Ile Arg Ser Ile Phe Arg Tyr Ala Gly Ala Pro Thr Glu Asp
        355                 360                 365

Pro Asp Thr Thr Gly Ser Leu Pro Ser Gly Cys Tyr Asp Glu Asp Val
    370                 375                 380
```

```
Val Pro Tyr Ala Lys Thr Thr Val Pro Gln Glu Met Pro Glu Gln Leu
385                 390                 395                 400

Ser Val Gly Phe Asn Pro Asn Trp Thr Ser Asp Val Thr Gln Asn Gln
                405                 410                 415

Gly Leu Val Gln Trp Leu Val Asn Gly Asn Pro Met Ala Val Asp Leu
            420                 425                 430

Glu Val Pro Thr Leu Gln Ser Val Leu Asp Gly Asn Val Thr Tyr Gly
        435                 440                 445

Asn Asn Arg His Val Phe Ala Val Asp Glu Lys His Gln Trp Gln Tyr
    450                 455                 460

Trp Val Ile Gln Gln Asn Ser Ser Asn Pro Pro Leu Pro His Pro Ile
465                 470                 475                 480

His Leu His Gly His Asp Phe Tyr Val Leu Ala Gln Val Glu Asn Ala
                485                 490                 495

Val Trp Asn Gly Asp Ile Ser Thr Leu Lys Thr Asp Asn Pro Ile Arg
                500                 505                 510

Arg Asp Thr Ala Asp Leu Pro Ala Gly Gly Tyr Leu Val Leu Ala Phe
            515                 520                 525

Glu Ser Asp Asn Pro Gly Ala Trp Leu Met His Cys His Ile Pro Phe
530                 535                 540

His Val Ala Ala Gly Leu Gly Val Gln Phe Leu Glu Arg Glu Ser Glu
545                 550                 555                 560

Ile Lys Ala Gln Asp Gly Tyr Ala Glu Met His Arg Thr Cys Ala Asn
                565                 570                 575

Trp Gln Ser Trp Arg Tyr Lys Tyr His Pro Asn Gly Ile Leu Phe Pro
            580                 585                 590

Gly Asp Ser Gly Leu Arg Arg Arg Asn
        595                 600

<210> SEQ ID NO 3
<211> LENGTH: 1983
<212> TYPE: DNA
<213> ORGANISM: Fusarium verticillioides

<400> SEQUENCE: 3
atggctctca tcgagcgagt atggcacgcc tgcgtcagta tagtcgcatg ctaacaatg      60 tggcccacat ctccatccac ctcctaccaa catcccttc gccccaacca tcctcacact     120
cacattgaag accccagccc tggcttccct atctttcatc cccgccagg tgatcatgag     180 ttcctctgcg agtacccaga atgacaggc tttgtgcaat gttcaatccc agagaacaga     240
gaatgttggc tgagacatcc tgatgggcga gagttcaaca ttcatactaa ctatgagaac     300
tttgcgccaa agggattat gaggcattat acgcttaata ttacggagag ttggtataat     360
gctgatgggc agaactttac ggaggcaaag ttgttcaatg gggagtatcc tgggccttgg     420
cttgaggctt gttggggaga tacgttcaac attaccgtca taacagtat gaagaggaat     480 ggcacaagta ttcactggca cggcattcgt cagaaccaga ccatggacat ggatggtgtc     540
aatggcatca ctcagtgtcc tattgcgcca ggtgatagct tcagctatat cttcaacacg     600
acgcagtacg gacgtcgtg gtatcatagc cactactctg tgcaatatgc agatggtctc     660
caaggcccca tcacaattca tggccctcaa tctgcacctt atgatgccac caagaggcca     720
ctgctcatga cagattggtc tcacgagagc gcattcagac tgctcttccc aggctctcaa     780
ttctccaaca agaccatcct tctcaacggc gcagcaacg tctcccacta cggctacacc     840
ccaactctgc ctatccctga taactatgag ttatacttca caaaactcc aaccgacaag     900
```

```
ccaactcgcc ccaagagata cctgctccgc ctgatcaata cttcatttga ctcaacactc    960
gtctttcca ttgataacca ctggcttcag atcgtcactt cagatttcgt tcccattgag   1020
ccgtacttca atacgtcggt gttgataggt atcggccaaa ggtacaacgt catcgttgaa   1080
gctaatcctc tgggcggtga tgtcaatgag attccagatg atggaaactt ctggataagg   1140
acgtgggtcg ctgatgcatg cggtatagcc ccaggaggag aaggctatga aaagaccggc   1200
atcctacgat acaaccactc cgacaaggct cttccatctt ctcaaccttg ggtcaacatc   1260
agcaaggctt gttctgatga gacttatact tcgctgagac ccaagattcc gtggtatatc   1320
ggcccagcgg ccaatgctca gaatggtgag aggttcaatg ttacttttga tccaaacgcc   1380
aagaatacgc ctgagttcca ggaagagtat ccagtcgcta cgtttggtct tcagagacct   1440
ggccagaact ttagaccact gcagattaat tactctgacc ctgttatgtt tcacttggac   1500
gaaccgaggg atacttaccc gccgaagtgg gtggtgatcc ggaagattaa tactgagaaa   1560
gaatgggtgt actttgttct cacgatagaa ggaatcagtg cgcgtactgg cgctcatccg   1620
attccctttc acggccatga cttcgctctt ctgcaacaag aagagaacca aacctacgac   1680
ccaagcaggc ttaacttgaa gcttgataat ccaccaagac gtgatgtcgt tctgctaccc   1740
cgcaatggct ttgtagtgat tgcgttcaag gccgataacc cgggtatctg gcttatgcac   1800
tgtcacattg cgcgccatgc ctctgaaggg ttggctatgc aggtcctgga gagacaggga   1860
gattcgaata agttgttccc tgttggatcg cccaatatga ttgaggcaga gagggtttgt   1920
aaagtttggg agacgtggat ggatggggag aaggatttct ttgagggtga ctctggtatt   1980
taa                                                                 1983
```

<210> SEQ ID NO 4
<211> LENGTH: 660
<212> TYPE: PRT
<213> ORGANISM: Fusarium verticillioides

<400> SEQUENCE: 4

```
Met Ala Leu Ile Glu Arg Val Trp His Ala Cys Val Ser Ile Ala
 1               5                  10                  15

Trp Leu Thr Met Trp Pro Thr Ser Pro Ser Thr Ser Tyr Gln His Pro
                20                  25                  30

Leu Arg Pro Asn His Pro His Thr His Ile Glu Asp Pro Ser Pro Gly
            35                  40                  45

Phe Pro Ile Phe His Pro Pro Gly Asp His Glu Phe Leu Cys Glu
        50                  55                  60

Tyr Pro Glu Met Thr Gly Phe Val Gln Cys Ser Ile Pro Glu Asn Arg
65                  70                  75                  80

Glu Cys Trp Leu Arg His Pro Asp Gly Arg Glu Phe Asn Ile His Thr
                85                  90                  95

Asn Tyr Glu Asn Phe Ala Pro Lys Gly Ile Met Arg His Tyr Thr Leu
            100                 105                 110

Asn Ile Thr Glu Ser Trp Tyr Asn Ala Asp Gly Gln Asn Phe Thr Glu
        115                 120                 125

Ala Lys Leu Phe Asn Gly Glu Tyr Pro Gly Pro Trp Leu Glu Ala Cys
    130                 135                 140

Trp Gly Asp Thr Phe Asn Ile Thr Val Ile Asn Ser Met Lys Arg Asn
145                 150                 155                 160

Gly Thr Ser Ile His Trp His Gly Ile Arg Gln Asn Gln Thr Met Asp
                165                 170                 175
```

-continued

```
Met Asp Gly Val Asn Gly Ile Thr Gln Cys Pro Ile Ala Pro Gly Asp
            180                 185                 190

Ser Phe Ser Tyr Ile Phe Asn Thr Thr Gln Tyr Gly Thr Ser Trp Tyr
            195                 200                 205

His Ser His Tyr Ser Val Gln Tyr Ala Asp Gly Leu Gln Gly Pro Ile
    210                 215                 220

Thr Ile His Gly Pro Gln Ser Ala Pro Tyr Asp Ala Thr Lys Arg Pro
225                 230                 235                 240

Leu Leu Met Thr Asp Trp Ser His Glu Ser Ala Phe Arg Leu Leu Phe
                245                 250                 255

Pro Gly Ser Gln Phe Ser Asn Lys Thr Ile Leu Leu Asn Gly Ala Gly
            260                 265                 270

Asn Val Ser His Tyr Gly Tyr Thr Pro Thr Leu Pro Ile Pro Asp Asn
            275                 280                 285

Tyr Glu Leu Tyr Phe Asn Lys Thr Pro Thr Asp Lys Pro Thr Arg Pro
    290                 295                 300

Lys Arg Tyr Leu Leu Arg Leu Ile Asn Thr Ser Phe Asp Ser Thr Leu
305                 310                 315                 320

Val Phe Ser Ile Asp Asn His Trp Leu Gln Ile Val Thr Ser Asp Phe
                325                 330                 335

Val Pro Ile Glu Pro Tyr Phe Asn Thr Ser Val Leu Ile Gly Ile Gly
            340                 345                 350

Gln Arg Tyr Asn Val Ile Val Glu Ala Asn Pro Leu Gly Gly Asp Val
            355                 360                 365

Asn Glu Ile Pro Asp Asp Gly Asn Phe Trp Ile Arg Thr Trp Val Ala
    370                 375                 380

Asp Ala Cys Gly Ile Ala Pro Gly Gly Glu Gly Tyr Glu Lys Thr Gly
385                 390                 395                 400

Ile Leu Arg Tyr Asn His Ser Asp Lys Ala Leu Pro Ser Ser Gln Pro
                405                 410                 415

Trp Val Asn Ile Ser Lys Ala Cys Ser Asp Glu Thr Tyr Thr Ser Leu
            420                 425                 430

Arg Pro Lys Ile Pro Trp Tyr Ile Gly Pro Ala Ala Asn Ala Gln Asn
            435                 440                 445

Gly Glu Arg Phe Asn Val Thr Phe Asp Pro Asn Ala Lys Asn Thr Pro
450                 455                 460

Glu Phe Gln Glu Glu Tyr Pro Val Ala Thr Phe Gly Leu Gln Arg Pro
465                 470                 475                 480

Gly Gln Asn Phe Arg Pro Leu Gln Ile Asn Tyr Ser Asp Pro Val Met
                485                 490                 495

Phe His Leu Asp Glu Pro Arg Asp Thr Tyr Pro Pro Lys Trp Val Val
            500                 505                 510

Ile Pro Glu Asp Tyr Thr Glu Lys Glu Trp Val Tyr Phe Val Leu Thr
            515                 520                 525

Ile Glu Gly Ile Ser Ala Arg Thr Gly Ala His Pro Ile His Leu His
    530                 535                 540

Gly His Asp Phe Ala Leu Leu Gln Gln Glu Glu Asn Gln Thr Tyr Asp
545                 550                 555                 560

Pro Ser Arg Leu Asn Leu Lys Leu Asp Asn Pro Pro Arg Arg Asp Val
                565                 570                 575

Val Leu Leu Pro Arg Asn Gly Phe Val Val Ile Ala Phe Lys Ala Asp
            580                 585                 590
```

-continued

```
Asn Pro Gly Ile Trp Leu Met His Cys His Ile Ala Arg His Ala Ser
        595                 600                 605

Glu Gly Leu Ala Met Gln Val Leu Glu Arg Gln Gly Asp Ser Asn Lys
        610                 615                 620

Leu Phe Pro Val Gly Ser Pro Asn Met Ile Glu Ala Glu Arg Val Cys
625                 630                 635                 640

Lys Val Trp Glu Thr Trp Met Asp Gly Glu Lys Asp Phe Phe Glu Gly
                645                 650                 655

Asp Ser Gly Ile
            660
```

LACCASES FOR BIO-BLEACHING

CROSS-REFERENCE TO RELATED APPLICATIONS

This application is a divisional of U.S. patent application Ser. No. 14/591,449, filed Jan. 7, 2015, which is a divisional of U.S. patent application Ser. No. 13/745,394, filed Jan. 18, 2013, now U.S. Pat. No. 8,951,766; which is a divisional of U.S. patent application Ser. No. 12/439,459, filed Sep. 23, 2009, now U.S. Pat. No. 8,377,670; which is a national stage filing of PCT/US2007/019124, filed Aug. 31, 2007; which claims priority to U.S. Provisional Application No. 60/824,402, filed Sep. 1, 2006.

PARTIES OF JOINT RESEARCH AGREEMENT

The subject matter disclosed herein is the subject of a joint research agreement between BASF Enzymes LLC, formerly known as "Verenium Corporation," and BASF Aktiengesellschaft.

REFERENCE TO SEQUENCE LISTING, TABLE, OR COMPUTER PROGRAM LISTING

The entire content of the following electronic submission of the sequence listing via the USPTO EFS-WEB server, as authorized and set forth in MPEP §1730 II.B.2(a)(C), is incorporated herein by reference into the specification in its entirety and for all purposes. The sequence listing is identified on the electronically filed .txt file as follows: "20160428SEQUENCE_LISTINGD2040-02ND3", created Apr. 28, 2016, which is 15.8 KB in size.

BACKGROUND OF THE INVENTION

Field of the Invention

The invention relates to the field of biochemistry. Provided herein are isolated laccase enzymes and nucleic acids encoding them. Also provided are mediators for laccase reactions. Also provided herein are methods for using laccases to oxidize lignins and other phenolic and aromatic compounds, such as for bio-bleaching and decolorization of wood pulp under high temperature and pH conditions to facilitate a substantial reduction in use of bleaching chemicals, as well as for treatment of fibers.

Description of the Related Art

Wood fiber is a multi-layered structure consisting primarily of cellulose, hemicellulose and lignin. Lignin is an insoluble complex polymer of phenolic compounds. Up to 90% of the lignin is solubilized and removed during the pulping process. The remaining lignin is a major cause of residual color in the pulp and must be removed by oxidative degradation or bleaching. The bleaching process requires application of harsh chemicals and conditions that are energy-intensive. Use of enzymes that assist in the bleaching process can allow reduced use of bleaching chemicals, increased energy efficiency of pulp plants, and have environmental benefits due to reduced chemical waste streams.

Filamentous fungi are able to efficiently degrade lignin by the action of several secreted enzyme classes. Of these, laccases have attracted considerable interest for application in pulp bio-bleaching. Laccases are multi-copper oxidases that couple direct oxidation of aromatic compounds with the reduction of molecular oxygen to water. During lignin degradation, laccases are thought to act on small phenolic lignin fragments that then react with the lignin polymer resulting in its degradation. Alternatively, artificial mediator compounds can be provided to accelerate the delignification process.

The wood pulping process can involve alkaline conditions. However, most known laccases are acidic enzymes. Only a few neutral or alkaline laccases have been reported; a laccase from *Rhus vernificera* has $pH_{opt}$ 9 and a laccase from *Melanocarpus albomyces* has a neutral $pH_{opt}$ on phenolic substrates. However, both of these laccases are only capable of oxidizing relatively low redox potential mediators that are not likely to oxidize lignin. Laccases are also likely to be exposed to relatively high temperatures in the pulp bio-bleaching application. Laccase enzymes that function well under the high temperature and pH conditions of typical pulping processes are desirable.

SUMMARY OF THE INVENTION

Some embodiments relate to laccase polypeptides. In particular, some embodiments relate to isolated polypeptides comprising, consisting essentially of, or consisting of, the amino acid sequence of SEQ ID NOs: 2 and 4.

Some embodiments provide variants of the laccase polypeptides. For example, some embodiments relate to isolated polypeptides, comprising, consisting essentially of, or consisting of an amino acid sequence having at least 80%, 85%, 90%, 95%, 96%, 97%, 98%, or 99% sequence identity to the amino acid sequence of the polypeptides of SEQ ID NOs: 2 and 4. In some embodiments, the isolated polypeptide has laccase activity, can oxidize lignin under conditions of pH greater than or equal to pH 8, and retains laccase activity for at least about 5 minutes at greater than or equal to 60° C.

Some embodiments relate to variants of SEQ ID NO: 4 that have at least one amino acid substitution, wherein the position of the at least one substitution in SEQ ID NO: 4 is selected from the group consisting of amino acid residue 162, 163, 164, 166, 168, 169, 170, 171, 172, 173, 174, 175, 176, 177, 178, 179, 180, 181, 182, 183, 184, 208, 210, 212, 213, 214, 215, 216, 218, 313, 314, 315, 316, 317, 318, 319, 320, 321, 351, 352, 353, 354, 452, 454, 470, 529, 530, 531, 532, 533, 534, 535, 536, 537, 538, 540, 541, 542, 545, 546, 547, 572, 573, 574, 575, 576, 577, 578, 579, 597, 598, 599, 603, 604, 605, 607, 608, 609, 610, 611, 612, 613, 614, 615, 616, 616, 618, 619, and 620, or any combination thereof.

In some embodiments, the laccase polypeptide variants lack its associated signal peptide, whereas in other embodiments, the laccase polypeptides or laccase polypeptide variants include a signal sequence.

Also provided herein are polynucleotides that encode the laccase polypeptides and laccase polypeptide variants disclosed herein. Some embodiments provide isolated polynucleotides that comprise, consist essentially of, or consist of a sequence that encodes the polypeptide of SEQ ID NO: 2 or 4, or variants thereof. For example, some embodiments relate to polynucleotides that comprise, consist essentially of, or consist of the nucleic acid sequence of SEQ ID NO: 1 or 3.

Some embodiments relate to laccase polynucleotide variants. Some embodiments provided herein provide polynucleotide sequences that share at least 80%, 85%, 90%, 95%, 96%, 97%, 98%, or 99% sequence identity to the polynucleotide of SEQ ID NO: 1 or 3, wherein said polynucleotide encodes a polypeptide has laccase activity, can oxidize lignin under conditions of pH greater than or equal to pH 8, and retains laccase activity for at least about 5 minutes at greater than or equal to 60° C.

Other embodiments relate to compounds that can mediate laccase reactions. These compounds are termed "mediators". Some embodiments relate to compounds represented by Formula I:

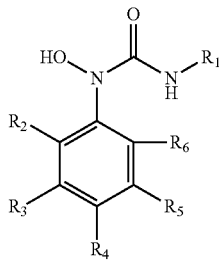

Formula (I)

wherein $R_1$, $R_2$, $R_3$, $R_4$, $R_5$ and $R_6$ can independently be H, $CH_3$, $CH_2CH_3$, $CH_2CH_2CH_3$, $CH(CH_3)_2$, $CH_2CH_2(CH_3)_2$, $C(CH_3)_3$, $CH_2CH_2CH_2$, $CH_3$, alkyl, aryl, phenyl, $CF_3$, $OC(CH_3)_3$, $OCH(CH_3)_2$, $CH_2CH_3$, $C(O)OCH_3$, COOH, $OCH_3$, OH, $OCF_3$, $NH_2$, $NH(CH_3)$, $N(CH_3)_2$, $CH_2NH_2$, $CH_2CH_2NH_2$, Br, or Cl. Exemplary compounds of Formula I provided herein include:

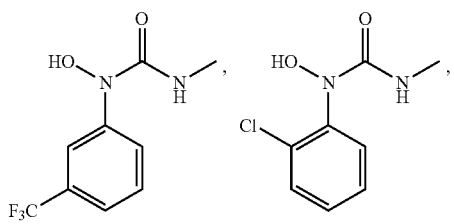

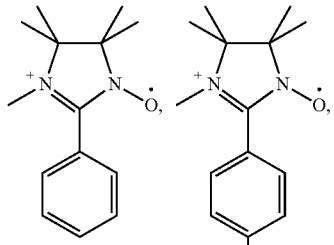

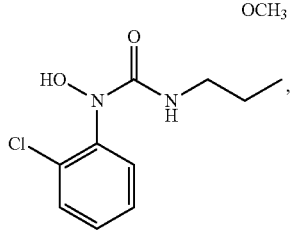

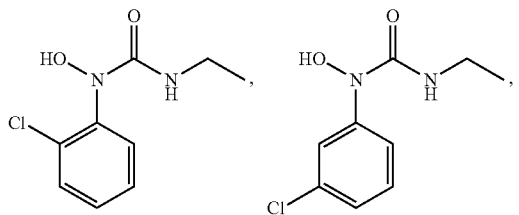

-continued

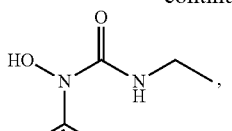

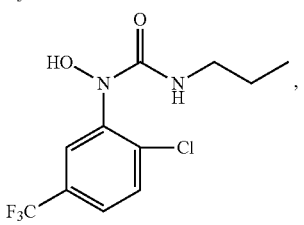

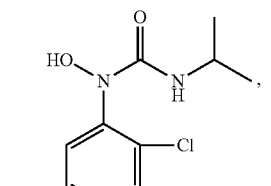

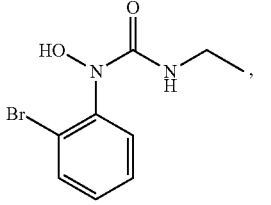

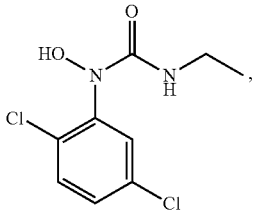

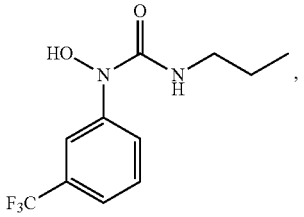

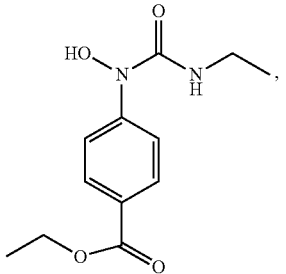

-continued

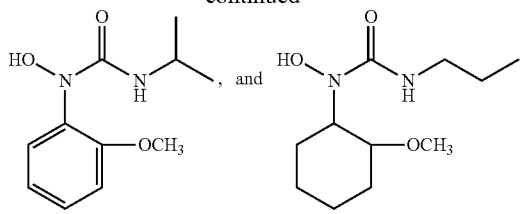

, and

Also provided herein are compounds represented by Formula II, A compound represented by Formula II:

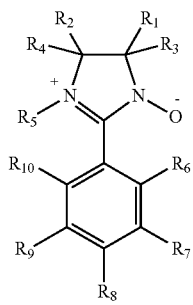

Formula (II)

wherein $R_1$, $R_2$, $R_3$, $R_4$, $R_5$, $R_6$, $R_7$, $R_8$, $R_9$ and $R_{10}$ are independently selected from the group consisting of H, $CH_3$, $CH_2CH_3$, $CH_2CH_2CH_3$, $CH(CH_3)_2$, $CH_2CH_2(CH_3)_2$, $C(CH_3)_3$, $CH_2CH_2CH_2$, $CH_3$, alkyl, aryl, phenyl, $CF_3$, $OC(CH_3)_3$, $OCH(CH_3)_2$, $CH_2CH_3$, $C(O)OCH_3$, COOH, $OCH_3$, OH, $OCF_3$, $NH_2$, $NH(CH_3)$, $N(CH_3)_2$, $CH_2NH_2$, $CH_2CH_2NH_2$, Br, and Cl.

Exemplary compounds of Formula II provided herein include:

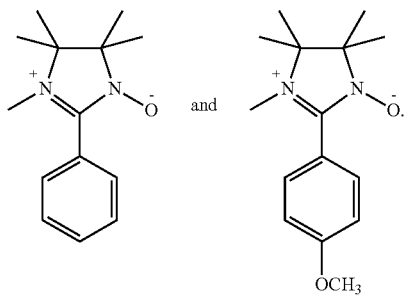

Also provided herein are methods for mediating the oxidation of a phenolic or aromatic substrate. In some embodiments, the method includes the step of contacting the phenolic or aromatic substrate with a compound represented by Formula I or Formula II, such as

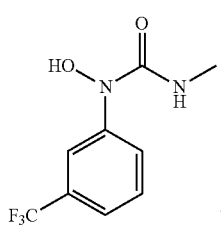

In some embodiments, the phenolic or aromatic substrate is also contacted with a mediator selected from the group consisting of violuric acid; 2,6,6-tetrarmethylpiperidein-1-yloxy (TEMPO); 1-hydroxybenzotriazole (HBT); 2,2'-azino-bis(3-ethylbenzthiazoline-6-sulfonic acid) (ABTS); syringaldazine; N-benzoyl-N-phenyl hydroxylamine (BPHA); N-hydroxyphthalimide, 3-Hydroxy-1,2,3-benzotriazin-4-one; promazine; 1,8-Dihydroxy-4,5-dinitroanthraquinone; phenoxazine; anthraquinone; 2-hydroxy-1,4-naphthoquinone; phenothiazine; anthrone; anthracene; anthrarufin; anthrarobin; dimethoxyphenol (DMP); ferulic acid; catechin; epicatechin; homovanillic acid (HMV); and 2,3-dihydroxybenzoic acid (2,3-DHB); or any combination thereof.

In some embodiments, the phenolic or aromatic substrate is also contacted with a laccase. For example, in some embodiments, the phenolic or aromatic substrate is contacted with a polypeptide that comprises, consists essentially of, or consists of the sequence of SEQ ID NO: 2 or SEQ ID NO: 4; or variants of SEQ ID NO: 2 or that have at least about 80%, at least about 85%, at least about 90%, at least about 95%, at least about 96%, at least about 97%, at least about 98%, or at least about 99% sequence identity to SEQ ID NO: 2 or 4, which can oxidize lignin under conditions of pH greater than or equal to pH 8, and retains laccase activity for at least about 5 minutes at greater than or equal to 60° C.

In some embodiments, the phenolic or aromatic substrate is also contacted with a mediator, such as a compound represented by Formula I or Formula II, for example

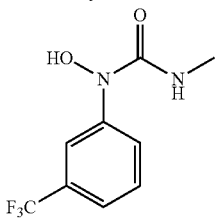

In some embodiments, the mediator can be violuric acid; 2,6,6-tetramethylpiperidein-1-yloxy (TEMPO); 1-hydroxybenzotriazole (HBT); 2,2-azinobis-(3-ethyl-benzothiazoline-6-sulfonate (ABTS); or syringaldazine.

Also provided herein are methods of delignifying a composition comprising lignin. In some embodiments, the method includes the step of contacting the lignin-comprising composition with an isolated polypeptide that comprises, consists essentially of, or consists of the polypeptide of SEQ ID NO: 2 or SEQ ID NO: 4, or variants thereof. For example, in some embodiments, the lignin-comprising composition is contacted with a polypeptide that has at least about 80%, 85%, 90%, 95%, 96%, 97%, 98%, or 99% sequence identity to SEQ ID NO: 2 or 4, and which can oxidize lignin under conditions of pH greater than or equal to pH 8, and retains laccase activity for at least about 5 minutes at greater than or equal to 60° C.

In some embodiments, the lignin-comprising composition is also contacted with a mediator, such as a compound represented by Formula I or Formula II, for example

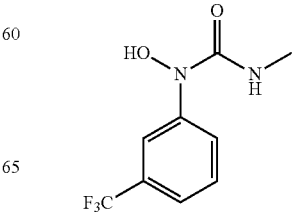

In some embodiments, the lignin-comprising composition is contacted with a mediator including one or more of the following compounds: violuric acid; 2,6,6-tetrarmethylpiperidein-1-yloxy (TEMPO); 1-hydroxybenzotriazole (HBT); 2,2'-azino-bis(3-ethylbenzthiazoline-6-sulfonic acid) (ABTS); syringaldazine; N-benzoyl-N-phenyl hydroxylamine (BPHA); N-hydroxyphthalimide; 3-Hydroxy-1,2,3-benzotriazin-4-one; promazine; 1,8-Dihydroxy-4,5-dinitroanthraquinone; phenoxazine; anthraquinone; 2-hydroxy-1,4-naphthoquinone; phenothiazine; anthrone; anthracene; anthrarufin; anthrarobin; dimethoxyphenol (DMP); ferulic acid; catechin; epicatechin; homovanillic acid (HMV); and 2,3-dihydroxybenzoic acid (2,3-DHB); or any combination thereof.

In some embodiments, the delignification reaction can proceed under alkaline conditions, such as at a pH of between 7.5 and 11.5, for example at about pH 8, pH 9, or pH 10.

In some embodiments, the delignification reaction can proceed at a temperature of at least about 50° C., for example, at least about 60° C., or at least about 70° C.

Also provided are methods of oxidizing a fiber-comprising composition. In some embodiments, the method includes the step of contacting the fiber-comprising composition with an isolated polypeptide that comprises, consists essentially of, or consists of the polypeptide of SEQ ID NO: 2 or SEQ ID NO: 4, or variants thereof. For example, in some embodiments, the fiber-comprising composition is contacted with a polypeptide that has at least about 80%, 85%, 90%, 95%, 96%, 97%, 98%, or 99% sequence identity to SEQ ID NO: 2 or 4, and which can oxidize lignin under conditions of pH greater than or equal to pH 8, and retains laccase activity for at least about 5 minutes at greater than or equal to 60° C.

In some embodiments, the fiber-comprising composition is also contacted with a mediator, such as a compound represented by Formula I or Formula II, for example

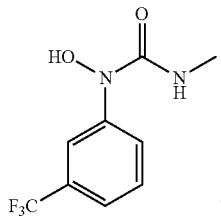

In some embodiments, the fiber-comprising composition is contacted with a mediator including one or more of the following compounds: violuric acid; 2,6,6-tetrarmethylpiperidein-1-yloxy (TEMPO); 1-hydroxybenzotriazole (HBT); 2,2'-azino-bis(3-ethylbenzthiazoline-6-sulfonic acid) (ABTS); syringaldazine; N-benzoyl-N-phenyl hydroxylamine (BPHA); N-hydroxyphthalimide, 3-Hydroxy-1,2,3-benzotriazin-4-one; promazine; 1,8-Dihydroxy-4,5-dinitroanthraquinone; phenoxazine; anthraquinone; 2-hydroxy-1,4-naphthoquinone; phenothiazine; anthrone; anthracene, anthrarufin, anthrarobin; dimethoxyphenol (DMP); ferulic acid; catechin; epicatechin; homovanillic acid (HMV); and 2,3-dihydroxybenzoic acid (2,3-DHB); or any combination thereof.

In some embodiments, the fiber oxidation reaction can proceed under alkaline conditions, such as at a pH of between 7.5 and 11.5, for example at about pH 8, pH 9, or pH 10.

In some embodiments, the fiber oxidation reaction can proceed at a temperature of at least about 50° C., for example, at least about 60° C., or at least about 70° C.

Also provided are methods of brightening or bleaching compositions comprising pulp or paper. In some embodiments, the method includes the step of contacting the composition comprising pulp or paper with an isolated polypeptide that comprises, consists essentially of, or consists of the polypeptide of SEQ ID NO: 2 or SEQ ID NO: 4, or variants thereof. For example, in some embodiments, the paper is contacted with a polypeptide that has at least about 80%, 85%, 90%, 95%, 96%, 97%, 98%, or 99% sequence identity to SEQ ID NO: 2 or 4, and which can oxidize lignin under conditions of pH greater than or equal to pH 8, and retains laccase activity for at least about 5 minutes at greater than or equal to 60° C.

In some embodiments, the composition comprising paper or pulp is also contacted with a mediator, such as a compound represented by Formula I or Formula II, for example

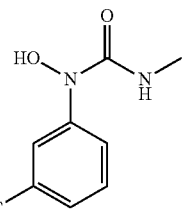

In some embodiments, the composition comprising paper or pulp is contacted with a mediator including one or more of the following compounds: violuric acid; 2,6,6-tetrarmethylpiperidein-1-yloxy (TEMPO); 1-hydroxybenzotriazole (HBT); 2,2'-azino-bis(3-ethylbenzthiazoline-6-sulfonic acid) (ABTS); syringaldazine; N-benzoyl-N-phenyl hydroxylamine (BPHA); N-hydroxyphthalimide, 3-Hydroxy-1,2,3-benzotriazin-4-one; promazine; 1,8-Dihydroxy-4,5-dinitroanthraquinone; phenoxazine; anthraquinone; 2-hydroxy-1,4-naphthoquinone; phenothiazine; anthrone; anthracene; anthrarufin; anthrarobin; dimethoxyphenol (DMP); ferulic acid; catechin; epicatechin; homovanillic acid (HMV); and 2,3-dihydroxybenzoic acid (2,3-DHB); or any combination thereof.

In some embodiments, the bleaching reaction can proceed under alkaline conditions, such as at a pH of between 7.5 and 11.5, for example at about pH 8, pH 9, or pH 10.

In some embodiments, the bleaching reaction can proceed at a temperature of at least about 50° C., for example, at least about 60° C., or at least about 70° C.

BRIEF DESCRIPTION OF THE DRAWINGS

(FIG. 5A), 60° C. (FIG. 5B), and 70° C. (FIG. 5C), measured as described in Example 6.

DETAILED DESCRIPTION OF THE PREFERRED EMBODIMENT

Figure 1:
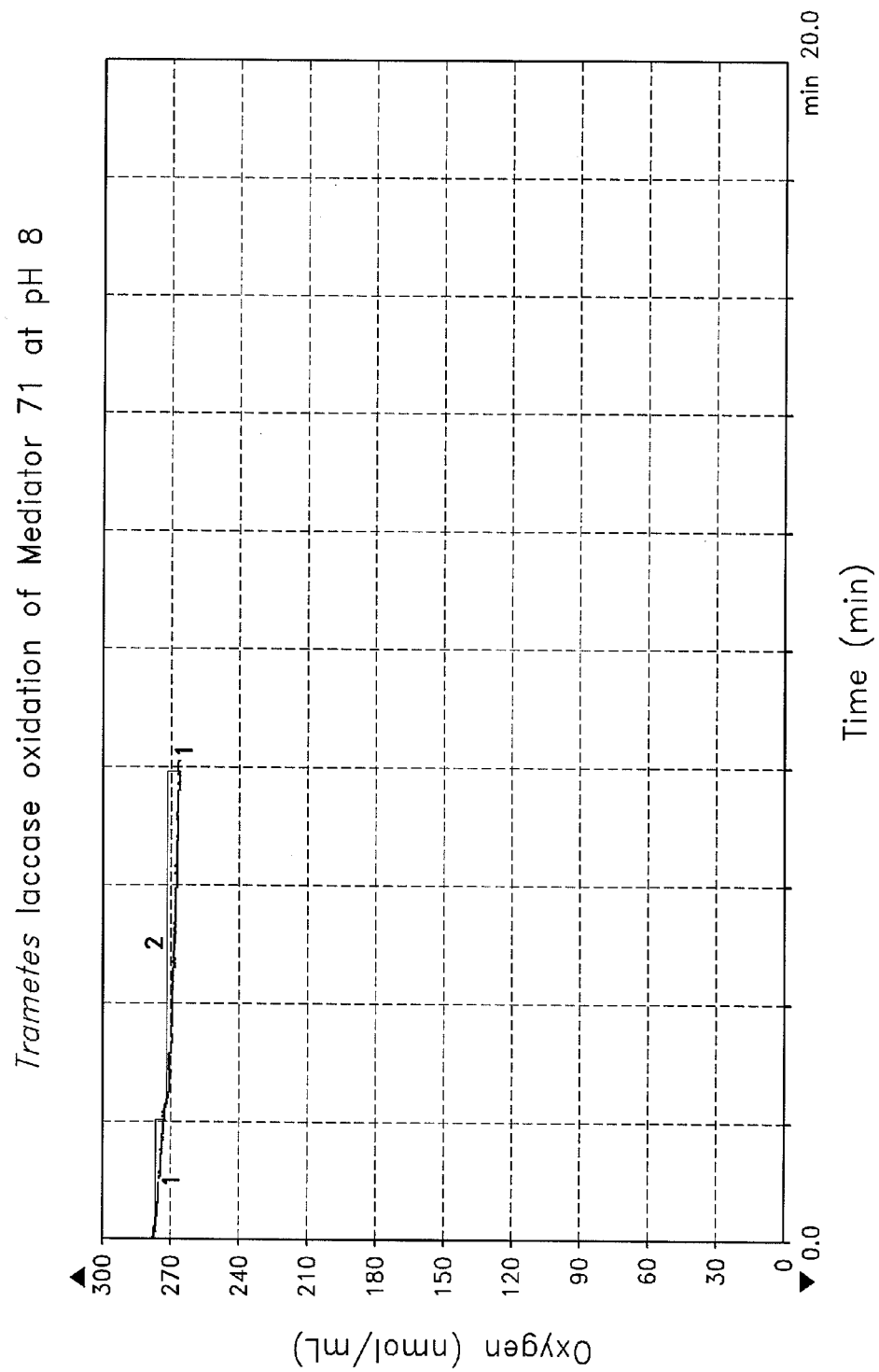
FIG. 1 is a graph showing the consumption of oxygen (nmol/mL) over time, indicative of oxidation of Mediator 71 at pH 8 by the *Trametes versicolor* laccase measured as described in Example 5.

Provided herein are laccases, polynucleotides encoding these enzymes, mediators for laccase or other oxidation reactions, and methods of using the laccases and mediators.

Laccases catalyze the oxidation of phenolic or other aromatic compounds with a concomitant reduction of oxygen to water (Malmstrom, B. G., "Early and more recent history in the research on multi-copper oxidases" in Multi-copper oxidases, ed Messercshmidt, A. (1997), World Scientific, Singapore). As used herein, the term "laccase" encompasses any polypeptide or enzyme having any laccase activity, for example, the oxidation and/or depolymerization of lignin, and/or the oxidation of 1-hydroxybenzotriazole (HBT), N-benzoyl-N-phenyl hydroxylamine (BPHA), N-hydroxyphthalimide, 3-hydroxy-1,2,3-benzotriazin-4-one, promazine, 1,8-dihydroxy-4,5-dinitroanthraquinone, phenoxazine, anthraquinone, 2-hydroxy-1,4-naphthoquinone, phenothiazine, syringaldazine, anthrone, anthracene, anthrarufin, anthrarobin, 2,2'-azino-bis(3-ethylbenzthiazoline-6-sulfonic acid) (ABTS), dimethoxyphenol (DMP), ferulic acid, catechin, epicatechin, homovanillic acid (HMV), 2,3-dihydroxybenzoic acid (2,3-DHB), 2,2,6,6-tetramethyl-piperidin-1-yloxy (TEMPO), dimethoxyphenol or dihydroxyfumaric acid (DHF) or equivalent compounds.

Polypeptides

Some embodiments provide polypeptides that have laccase activity, i.e., "laccase polypeptides" such as polypeptides that comprise, consist essentially of, or consist of polypeptides of SEQ ID NO: 2, SEQ ID NO: 4, or variants thereof, i.e., laccase variants. "Laccase polypeptide variant" means an active laccase polypeptide as defined above or below having at least about 80% amino acid sequence identity with a full-length laccase polypeptide sequence as disclosed herein (e.g., SEQ ID NO: 2, SEQ ID NO: 4, or variants thereof) or any fragment of a laccase polypeptide sequence as disclosed herein. Such laccase polypeptide variants include, for instance, laccase polypeptides wherein one or more amino acid residues are added, or deleted, at the N- or C-terminus of the full-length laccase amino acid sequence. Ordinarily, a laccase polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length laccasse polypeptide sequence as disclosed herein (e.g., SEQ ID NO: 2 or SEQ ID NO: 4) or any other specifically defined fragment of a full-length laccase polypeptide sequence as disclosed herein. Ordinarily, laccase variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, or more.

"Percent (%) amino acid sequence identity" with respect to the laccase polypeptide sequences identified herein is defined as the percentage of amino acid residues in a candidate sequence that are identical with the amino acid residues in the specific laccase polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is available as described herein. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that programs alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, demonstrated herein is a method to calculate the % amino acid sequence identity of the amino acid sequence designated A Comparison Protein to the amino acid sequence designated laccase, wherein "laccase" represents the amino acid sequence of a hypothetical laccase polypeptide of interest, "Comparison Protein" represents the amino acid sequence of a polypeptide against which the "laccase" polypeptide of interest is being compared, and "X, "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the laccase polypeptide of interest having a sequence derived from the laccase polypeptide and the comparison amino acid sequence of interest (i.e., the sequence against which the laccase polypeptide of interest is being compared which may be a laccase variant polypeptide) as determined by WU-BLAST-2 by (b) the total number of amino acid residues of the laccase polypeptide of interest. For example, in the statement a polypeptide comprising an the amino acid sequence A which has or having at least 80% amino acid sequence identity to the amino acid sequence B, the amino acid sequence A is the comparison amino acid sequence of interest and the amino acid sequence B is the amino acid sequence of the laccase polypeptide of interest.

Percent amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Optionally the variation is by substitution of at least one amino acid with any other amino acid in one or more of the domains of the polypeptide. Guidance in determining which amino acid residue may be inserted, substituted or deleted without adversely affecting the desired activity may be found by comparing the sequence of the polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

In particular embodiments, conservative substitutions of interest are shown below under the heading of preferred substitutions. If such substitutions result in a change in biological activity, then more substantial changes, denominated exemplary substitutions shown below, or as further described below in reference to amino acid classes, are introduced and the products screened.

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Preferred embodiments provide laccase variants of SEQ ID NO: 4 that have one or more amino acid substitutions such that the residues at positions 162, 163, 164, 166, 168, 169, 170, 171, 172, 173, 174, 175, 176, 177, 178, 179, 180, 181, 182, 183, 184, 208, 210, 212, 213, 214, 215, 216, 218, 313, 314, 315, 316, 317, 318, 319, 320, 321, 351, 352, 353, 354, 452, 454, 470, 529, 530, 531, 532, 533, 534, 535, 536, 537, 538, 540, 541, 542, 545, 546, 547, 572, 573, 574, 575, 576, 577, 578, 579, 597, 598, 599, 603, 604, 605, 607, 608, 609, 610, 611, 612, 613, 614, 615, 616, 616, 618, 619, or 620, or any combination thereof, in SEQ ID NO:4 are changed to any other amino acid.

In some embodiments, the laccase variants lack signal sequences. For example, provided are laccase variants of SEQ ID NO: 2 and SEQ ID NO: 4 that lack or contain their associated signal sequence, or signal peptide. The associated signal peptide for SEQ ID NO: 2 has been tentatively identified as residues 1-22. The associated signal peptide for SEQ ID NO: 4 has tentatively been identified as residues 1-26. It is noted, however, that the C-terminal boundary of the signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. Accordingly, some embodiments provide these polypeptides, and the polynucleotides encoding them. As such, for purposes of the present application, the signal peptide of the laccase polypeptide of SEQ ID NO: 2 extends from amino acids 1 to X of SEQ ID NO: 2, wherein X is any amino acid from 1 to 27 of SEQ ID NO: 2. Therefore, mature forms of the variants of SEQ ID NO: 2 provided herein are polypeptides comprising amino acids X to 601 of SEQ ID NO: 2, wherein X is any amino acid from 1 to 27 of SEQ ID NO: 2 and variants thereof. Similarly, for purposes of the present application, the signal peptide of the laccase polypeptide of SEQ ID N: 4 extends from amino acids 1 to X of SEQ ID NO: 4, wherein X is any amino acid from 1 to 31 of SEQ ID NO: 4, and variants thereof. Mature forms of the variants of SEQ ID NO: 4 provided herein are polypeptides comprising amino acids X to 660 of SEQ ID NO: 4, wherein X ix any amino acid from 1 to 31 of SEQ ID NO: 4.

In some embodiments, the variant polypeptides provided herein have increased laccase activity compared to the wild-type counterpart, e.g., SEQ ID NO: 2 or SEQ ID NO: 4, under specified conditions. In some embodiments, the variant polypeptides have decreased activity compared to the wild-type counterpart under specified conditions. In some embodiments, the activity of the variant laccase is altered, such that it exhibits increased activity under one set of conditions, and decreased activity under another set of conditions. Non-limiting examples of activities that may be altered in laccase variants compared to their wild-type counterparts provided herein include pH optimum, thermostability, redox potential, and enzyme kinetics. For example, in some embodiments, the laccase variants exhibit increased activity at pH 7, pH 8, pH 9, pH 10, or above, or any number in between, compared to the wild-type counterpart, e.g., SEQ ID NO: 2 or SEQ ID NO: 4. In some embodiments, the laccase variants exhibit increased thermostability compared to the wild-type counterpart, e.g., SEQ ID NO: 2 or SEQ ID NO: 4. For example, in some embodiments, the laccase variant retains activity for an increased period of time, e.g., 1 minute, 5 minutes, 10 minutes, 15 minutes, 20 minutes, 30 minutes, 40 minutes, 50 minutes, 60 minutes, or longer at temperatures above room temperature, compared to the wild-type counterpart, e.g., SEQ ID NO: 2 or SEQ ID NO: 4. In some embodiments, the laccase variant exhibits an increased redox potential as compared to its wild-type counterpart e.g., SEQ ID NO: 2 or SEQ ID NO: 4.

In preferred embodiments, the laccase polypeptides and laccase polypeptide variants disclosed herein exhibit optimal activity at alkaline pH, e.g., at about pH 7.25, pH 7.5, pH 7.75, pH 8.0, pH 8.25, pH 8.5, pH 8.75, pH 9.0, pH 9.25, pH 9.5, pH 9.75, pH 10, pH 10.25, pH 10.5, pH 10.75, pH 11, pH 11.25, pH 11.5, or above. For example, the laccases or laccase variants may have an alkaline pH optimum for oxidation of mediators such as compounds of Formula I or Formula II, discussed below, or any mediator now known or discovered in the future, for example, violuric acid; 2,6,6-tetrarmethylpiperidein-1-yloxy (TEMPO); 1-hydroxybenzotriazole (HBT); 2,2'-azino-bis(3-ethylbenzthiazoline-6-sulfonic acid) (ABTS); syringaldazine; N-benzoyl-N-phenyl hydroxylamine (BPHA); N-hydroxyphthalimide, 3-Hydroxy-1,2,3-benzotriazin-4-one; promazine; 1,8-Dihydroxy-4,5-dinitroanthraquinone; phenoxazine; anthraquinone; 2-hydroxy-1,4-naphthoquinone; phenothiazine; anthrone; anthracene, anthrarufin, anthrarobin, dimethoxyphenol (DMP); ferulic acid; catechin; epicatechin; homovanillic acid (HMV); and 2,3-dihydroxybenzoic acid (2,3-DHB); and the like. Preferably, the laccases and laccase variants can oxidize mediators with higher redox potentials such as violuric acid, TEMPO, Mediator 71 (described herein), ore mediators with higher redox potentials at pH 8 and above.

Preferably, laccase polypeptides and laccase polypeptide variants are thermostable, and retain laccase activity at temperatures above about 22° C., e.g., above about 25° C., 30° C., 35° C., 40° C., 45° C., 50° C., 55° C., 60° C., 65° C., 70° C., 80° C., 85° C., 90° C., 95° C., or higher. In some embodiments, the laccase polypeptides retain laccase activity for at least about 1 minute, 2 minutes, 3 minutes, 5 minutes, 10 minutes 15 minutes, 20 minutes, 25 minutes, 30 minutes, 35 minutes, 40 minutes, 45 minutes, 50 minutes, 60 minutes, 70 minutes, 80 minutes, 90 minutes, 100 minutes, or more or any number in between at temperatures above about 22° C., e.g., at about 65° C., 70° C., 80° C., or above.

Polynucleotides

Also provided herein are laccase polynucleotides. As used herein, "laccase polynucleotides" refer to polynucleotides that encode laccase polypeptides. For example, laccase polynucleotides include polynucleotides that comprise, consist essentially of, or consist of the sequences of SEQ ID NO: 1, SEQ ID NO: 3, or variants or fragments thereof.

"Laccase variant polynucleotide" or "laccase variant nucleic acid sequence" means a nucleic acid molecule which encodes an active laccase polypeptide as defined below and which has at least about 80% nucleic acid sequence identity with a nucleotide acid sequence encoding a full-length laccase polypeptide sequence as disclosed herein, a full-length laccase polypeptide sequence lacking the signal peptide as disclosed herein, an extracellular domain of a laccase polypeptide, with or without the signal peptide, as disclosed herein or any other fragment of a full-length laccase polypeptide sequence as disclosed herein. Ordinarily, a laccase variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence laccase polypeptide sequence as disclosed herein or any other fragment of a full-length laccase polypeptide sequence as disclosed herein.

Ordinarily, laccase variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to laccase-encoding nucleic acid sequences identified herein is defined as the percentage of nucleotides in a candidate sequence that are identical with the nucleotides in the laccase nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "laccase DNA" wherein "laccase-DNA" represents a hypothetical OspA-encoding nucleic acid sequence of interest, "Comparison DNA" represents the nucleotide sequence of a nucleic acid molecule against which the "laccase-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the laccase polypeptide-encoding nucleic acid molecule of interest having a sequence derived from the native sequence laccase polypeptide-encoding nucleic acid and the comparison nucleic acid molecule of interest (i.e., the sequence against which the laccase polypeptide-encoding nucleic acid molecule of interest is being compared which may be a variant laccase polynucleotide) as determined by WU-BLAST-2 by (b) the total number of nucleotides of the laccase polypeptide-encoding nucleic acid molecule of interest. For example, in the statement Aan isolated nucleic acid molecule comprising a nucleic acid sequence A which has or having at least 80% nucleic acid sequence identity to the nucleic acid sequence B, the nucleic acid sequence A is the comparison nucleic acid molecule of interest and the nucleic acid sequence B is the nucleic acid sequence of the laccase polypeptide-encoding nucleic acid molecule of interest.

Percent nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program=s alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

Variations in the sequence of the polypeptides described herein, can be made, for example, using any of the techniques and guidelines for conservative and non-conservative mutations set forth, for instance, in U.S. Pat. No. 5,364,934. Variations may be a substitution, deletion or insertion of one or more codons encoding the polypeptide that results in a change in the amino acid sequence of the polypeptide as compared with the native sequence polypeptide.

In other embodiments, laccase variant polynucleotides are nucleic acid molecules that encode an active laccase polypeptide and which are capable of hybridizing, preferably under stringent hybridization and wash conditions, to nucleotide sequences encoding a full-length laccase polypeptide as disclosed herein, laccase variant polypeptides may be those that are encoded by an laccase variant polynucleotide.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

Variant laccase polynucleotides are generated using any technique known to those skilled in the art, such as saturation mutagenesis, optimized directed evolution, or the like. Gene Site Saturation Mutagenesis™, or "GSSM™." includes a method that uses degenerate oligonucleotide primers to introduce point mutations into a polynucleotide, described in detail in U.S. Pat. No. 6,673,552. Optimized directed evolution includes a method for reassembling fragments of related nucleic acid sequences, e.g., related genes, and explained in detail, in U.S. Pat. No. 6,361,974 and U.S. patent application Ser. No. 09/332,835.

"Isolated," when used to describe the various polypeptides disclosed herein, means polypeptide that has been identified and separated and/or recovered from a component of its natural environment. An "isolated" nucleic acid, such as an isolated laccase polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells Vectors and Host Cells Also provided are expression vectors and cloning vehicles comprising nucleic acids disclosed herein, e.g., sequences encoding laccase polypeptides, e.g. SEQ ID NO: 2, SEQ ID NO: 4, and variants thereof. Expression vectors and cloning vehicles can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *Bacillus, Aspergillus* and yeast). Vectors can include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXTI, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the embodiments described herein. The expression vector can comprise a promoter, a ribosome binding site for translation initiation and a transcription terminator. The vector can also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements. In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers. Vectors for expressing the polypeptide or fragment thereof in eukaryotic cells can also contain enhancers to increase expression levels. Examples include the SV40 enhancer on the late side of the replication origin bp 100 to 270, the cytomegalovirus early promoter enhancer, the polyoma enhancer on the late side of the replication origin, and the adenovirus enhancers.

Nucleic acid sequences disclosed herein can be inserted into a vector by a variety of procedures. In general, the sequence can be ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art. The vector can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook. Any vector may be used as long as it is replicable and viable in the host cell. Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNHlo6a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXTI, pSG (Stratagene) pSVK3, pBPV, pMSG, and pSVL (Pharmacia). Several fungal expression vectors are known to those skilled in the art and useful in the embodiments described herein, for example, those described in Campbell et al. Fungal Genetics Newsl. 36:79-81. However, any other vector may be used as long as it is replicable and viable in the host cell.

Nucleic acids disclosed herein can be expressed in expression cassettes, vectors or viruses and transiently or stably expressed in plant cells and seeds. One exemplary transient expression system uses episomal expression systems, e.g., cauliflower mosaic virus (CaMV) viral RNA generated in the nucleus by transcription of an episomal mini-chromosome containing supercoiled DNA, see, e.g., Covey (1990) Proc. Natl. Acad. Sci. USA 87:1633-1637. Alternatively, coding sequences, i.e., all or sub-fragments of sequences of the nucleic acids disclosed herein can be inserted into a plant host cell genome becoming an integral part of the host chromosomal DNA. Sense or antisense transcripts can be expressed in this manner.

A vector comprising the sequences (e.g., promoters or coding regions) from nucleic acids disclosed herein can comprise a marker gene that confers a selectable phenotype on a plant cell or a seed. For example, the marker may encode biocide resistance, particularly antibiotic resistance, such as resistance to kanamycin, G418, bleomycin, hygromycin, or herbicide resistance, such as resistance to chlorosulfuron or Basta. Expression vectors capable of expressing nucleic acids and proteins in plants are well known in the art, and can include, e.g., vectors from *Agrobacterium* spp., potato virus X (see, e.g., Angell (1997) EMBO J. 16:3675-3684), tobacco mosaic virus (see, e.g., Casper (1996) Gene 173:69-73), tomato bushy stunt virus (see, e.g., Hillman (1989) Virology 169:42-50), tobacco etch virus (see, e.g., Dolja (1997) Virology 234:243-252), bean golden mosaic virus (see, e.g., Morinaga (1993) Microbiol Immunol. 37:471-476), cauliflower mosaic virus (see, e.g., Cecchini (1997) Mol. Plant Microbe Interact. 10:1094-1101), maize Ac/Ds transposable element (see, e.g., Rubin (1997) Mol. Cell. Biol. 17:6294-6302; Kunze (1996) Curr. Top. Microbiol. Immunol. 204:161-194), and the maize suppressor-mutator (Spm) transposable element (see, e.g., Schlappi (1996) Plant Mol. Biol. 32:717-725); and derivatives thereof. In some embodiments, the expression vector can have two replication systems to allow it to be maintained in two organisms, for example in mammalian or insect cells for expression and in a prokaryotic host for cloning and amplification. Furthermore, for integrating expression vectors, the expression vector can contain at least one sequence homologous to the host cell genome. It can contain two homologous sequences which flank the expression construct. The integrating vector can be directed to a specific locus in the host cell by selecting the appropriate homologous sequence for inclusion in the vector. Constructs for integrating vectors are well known in the art.

Expression vectors disclosed herein may also include a selectable marker gene to allow for the selection of bacterial strains that have been transformed, e.g., genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways. The terms "vector" and "expression cassette" as used herein can be used interchangeably and refer to a nucleotide sequence which is capable of affecting expression of a nucleic acid, e.g., a mutated nucleic acid of the invention. Expression cassettes can include at least a promoter operably linked with the polypeptide coding sequence; and, optionally, with other sequences, e.g., transcription termination signals. Additional factors necessary or helpful in effecting expression may also be used, e.g., enhancers. "Operably linked" as used herein refers to linkage of a promoter upstream from a DNA sequence such that the promoter mediates transcription of the DNA sequence. Thus, expression cassettes also include plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and includes both the expression and non-expression plasmids.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. Current Protocols in Molecular Biology, John Wiley 503 Sons, Inc. 1997 and Sambrook et al., Molecular Cloning: A Laboratory Manual 2nd Ed. Cold Spring Harbor Laboratory Press (1989). Such procedures and others are deemed to be within the scope of those skilled in the art. The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus and pseudorabies. A variety of cloning and expression vectors for use with prokaryotic and eukaryotic hosts are described by Sambrook, et al, Molecular Cloning: A Laboratory Manual, 2nd Ed., Cold Spring Harbor, N.Y., (1989).

Also provided herein are transformed cells that comprise a nucleic acid sequence of the embodiments described herein, e.g., a sequence encoding a laccase polypeptide or variant described herein, or an expression cassette, e.g., a vector, of the described herein. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Lactococcus lactis, Streptomyces, Bacillus subtilis, Bacillus cereus, Salmonella typhimurium* or any species within the genera *Bacillus, Streptomyces* and *Staphylococcus*. Exemplary insect cells include *Drosophila* S2 and *Spodoptera* Sf9. Exemplary yeast cells include *Pichia pastoris, Saccharomyces cerevisiae* or *Schizosaccharomyces pombe*. Preferably, the host cell is a fungal cell. Exemplary fungal cells include species of *Aspergilllus*, e.g. *A. niger*, species of *Neurospora*, e.g., *N. crassa*, and the like. Exemplary animal cells include CHO, COS or Bowes melanoma or any mouse or human cell line. The selection of an appropriate host is within the abilities of those skilled in the art. Techniques for transforming a wide variety of higher plant species are well known and described in the technical and scientific literature. See, e.g., Weising (1988) Ann. Rev. Genet. 22:421-477, U.S. Pat. No. 5,750,870. The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, L, Basic Methods in Molecular Biology, (1986)). In one aspect, the nucleic acids or vectors of the invention are introduced into the cells for screening, thus, the nucleic acids enter the cells in a manner suitable for subsequent expression of the nucleic acid. The method of introduction is largely dictated by the targeted cell type. Exemplary methods include $CaPO_4$ precipitation, liposome fusion, lipofection (e.g., LIPOFECTIN™), electroporation, viral infection, etc. The candidate nucleic acids may stably integrate into the genome of the host cell (for example, with retroviral introduction) or may exist either transiently or stably in the cytoplasm (i.e. through the use of traditional plasmids, utilizing standard regulatory sequences, selection markers, etc.).

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue. Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof, hi some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof. The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*. Host cells containing the polynucleotides of interest, e.g., nucleic acids of the invention, can be cultured in conventional nutrient media modified as appropriate for activating promoters, selecting transformants or amplifying genes. The culture conditions, such as temperature, pH and the like, are those previously used with the host cell selected for expression and will be apparent to the ordinarily skilled artisan.

Also provided are methods for overexpressing recombinant laccase polypeptides in a cell comprising expressing a vector comprising a nucleic acid disclosed herein, e.g., a nucleic acid comprising a nucleic acid sequence with at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to SEQ ID NO: 1 or SEQ ID NO: 3 over a region of at least about 100 residues, or more, as described above.

Expression or overexpression of the laccase polypeptides can be effected by any means, e.g., use of a high activity promoter, a dicistronic vector or by gene amplification of the vector. The polypeptides encoded by the nucleic acids disclosed herein can be expressed, or overexpressed, in any in vitro or in vivo expression system. Any cell culture systems can be employed to express, or over-express, recombinant protein, including bacterial, insect, yeast, fungal or mammalian cultures. Over-expression can be effected by appropriate choice of promoters, enhancers, vectors (e.g., use of replicon vectors, dicistronic vectors (see, e.g., Gurtu (1996) Biochem. Biophys. Res. Commun. 229:295-8), media, culture systems and the like. In one aspect, gene amplification using selection markers, e.g., glutamine synthetase (see, e.g., Sanders (1987) Dev. Biol. Stand. 66:55-63), in cell systems are used to overexpress the polypeptides of the invention.

Mediators

In some instances, laccases function to oxidize substrates to yield a stabilized radical that can abstract a hydrogen from another organic molecule, such that the initial substrate returns to the ground state. In this case, the initial substrate is referred to as a mediator, and the final product of the reaction is the oxidized form of the second organic compound, e.g., oxidation of lignin. Accordingly, as used herein, the term "mediator" refers to any compound that can be oxidized by a laccase, and in turn oxidize another organic substrate.

Some mediators useful in the embodiments described herein are known to those skilled in the art. Non-limiting examples of known mediators violuric acid; 2,6,6-tetrarm-ethylpiperidein-1-yloxy (TEMPO); 1-hydroxybenzotriazole (HBT); 2,2'-azino-bis(3-ethylbenzthiazoline-6-sulfonic acid) (ABTS); syringaldazine; N-benzoyl-N-phenyl hydroxylamine (BPHA); N-hydroxyphthalimide; 3-Hydroxy-1,2,3-benzotriazin-4-one; promazine; 1,8-Dihydroxy-4,5-dinitroanthraquinone; phenoxazine; anthraquinone; 2-hydroxy-1,4-naphthoquinone; phenothiazine; anthrone; anthracene; anthrarufin; anthrarobin; dimethoxyphenol (DMP); ferulic acid; catechin; epicatechin; homovanillic acid (HMV); and 2,3-dihydroxybenzoic acid (2,3-DHB). However, it will be appreciated that mediators discovered in the future are also useful in the embodiments described herein.

Some embodiments provide the following mediators capable of mediating laccase reactions, such as compounds of Formula I and Formula II:

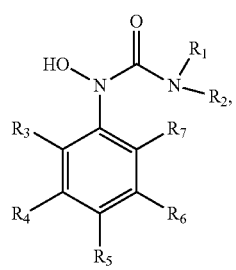

(Formula I)

wherein $R_1$ to $R_7$ are independently selected from the group consisting of H, $CH_3$, $CH_2CH_3$, $CH_2CH_2CH_3$, $CH(CH_3)_2$, $CH_2CH_2(CH_3)_2$, $C(CH_3)_3$, $CH_2CH_2CH_2$, $CH_3$, alkyl, aryl, hetaryl, phenyl, $CF_3$, $OC(CH_3)_3$, $OCH(CH_3)_2$, $CH_2CH_3$, $C(O)OCH_3$, $C(O)OC_2H_5$, $C(O)OC_3H_7$, $C(O)OCH(CH_3)_2$ COOH, $OCH_3$, OH, $OCF_3$, $NH_2$, $NH(CH_3)$, $N(CH_3)_2$, $C_2NH_2$, $CH_2CH_2NH_2$, Br, and Cl.

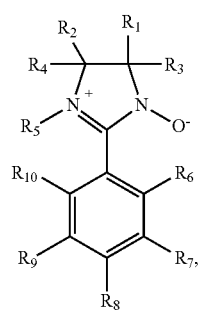

(Formula II)

wherein $R_1$ to $R{10}$ are independently selected from the group consisting of H, $CH_3$, $CH_2CH_3$, $CH_2CH_2CH_3$, $CH(CH_3)_2$, $CH_2CH_2(CH_3)_2$, $C(CH_3)_3$, $CH_2CH_2CH_2$, $CH_3$, alkyl, aryl, phenyl, $CF_3$, $OC(CH_3)_3$, $OCH(CH_3)_2$, $CH_2CH_3$, $C(O)OCH_3$, COOH, $OCH_3$, OH, $O^-$, $OCF_3$, $NH_2$, $NH(CH_3)$, $N(CH_3)_2$, $CH_2NH_2$, $CH_2CH_2NH_2$, Br, and Cl.

Preferred mediators include the following:

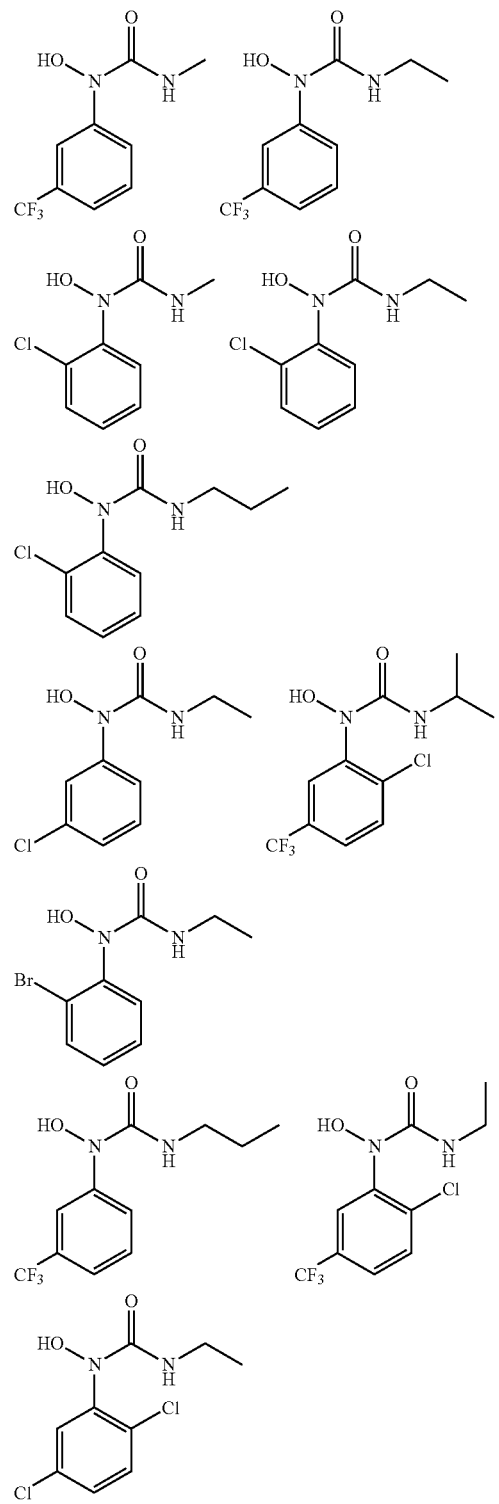

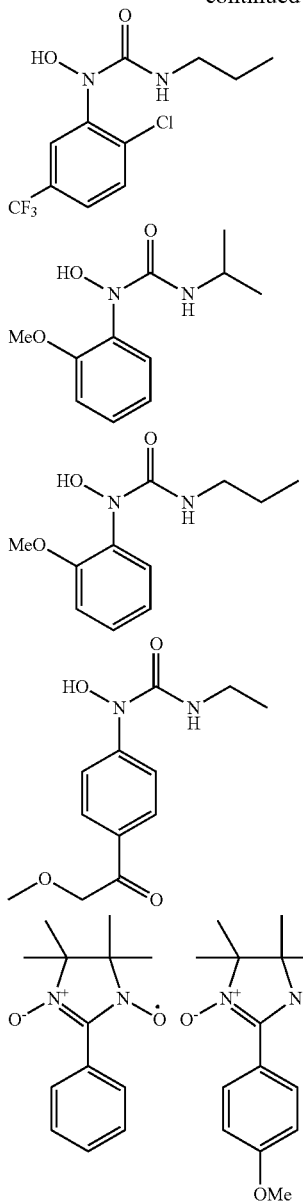

Most preferably,

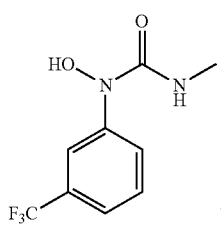

(Mediator 71)

Mediators disclosed herein can be synthesized from commercially available starting materials, using routine chemical synthesis techniques. For example, mediators of Formula I can be synthesized starting from hydroxylamines of formula A by reacting either with an isocyanate of formula B or a carbamic acid chlorides of formula C to afford hydroxyl ureas of formula I following known procedures (e.g. Crumbliss, J. Org. Chem. 1982(47) 1171; Tandon, J. Chem. Eng. Data. 1967(12) 143).

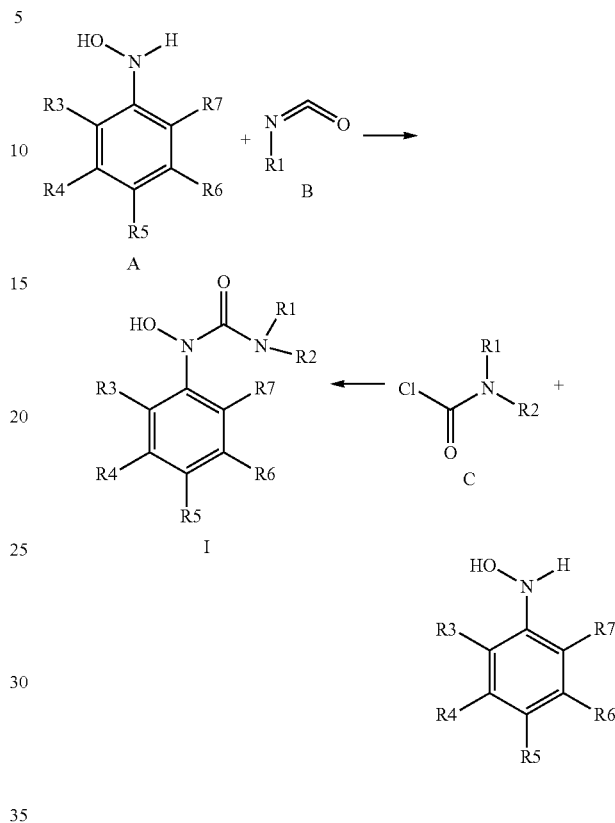

Example 1

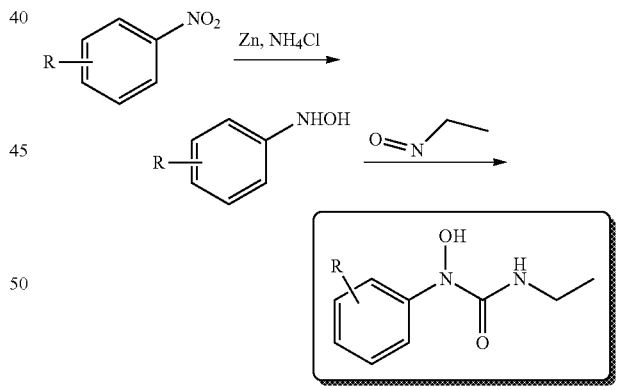

I. Preparation of N-(2-Chlorophenyl)Hydroxylamine

A suspension of 2-chloronitrobenzene (50 g, 0.318 mol) and ammonium chloride (16.9 g, 0.318 mmol) in 636 mL of water was warmed to 65° C. To the mixture was added in portions zinc (60 g, 0.955 mol) over 20 min, and the temperature was kept at 70° C.-75° C. After stirring for 10 min, TLC showed the reaction was completed. The mixture was filtered and washed with water (~70° C.). To the filtrate was added NaCl, then cooled to −10° C. After 1 h, the mixture was filtered and washed with pertrolume, and then dried to afford the desired hydroxylamine as a white solid (35 g, 76.9%), which was used to next step without purification. $^1$HNMR (400 MHz, DMSO): δ 8.36 (s, 2H), 7.16 (m, 2H), 6.79 (m, 2H).

II. Preparation of 1-(2-Chlorophenyl)-3-Ethyl-1-Hydroxyourea

To a solution of the hydroxylamine (35 g, 0.244 mol) in 1000 mL of CHCl$_3$ was added compound ethyl isocyanate (17.3 g, 0.244 mol) dropwise at −10° C. After addition, TLC showed the reaction was completed. The solution was concentrated and crystallized to the desired hydroxyurea as a white solid. $^1$HNMR (400 MHz, DMSO): δ 10.12 (s, 1H), 7.55 (m, 2H), 7.29 (m, 2H), 3.27 (q, 2H), 1.04 (t, 3H).

The Preparation of 1-(3-trifluoromethylphenyl)-3-ethyl-1-hydroxyourea followed the same procedure.

$^1$HNMR (400 MHz, DMSO): δ 10.40 (s, 1H), 7.91 (s, 1H), 7.78 (m, 1H), 7.46 (m, 2H), 7.27 (m, 1H), 3.13 (q, 2H), 1.03 (t, 3H).

Compounds of Formula II can be synthesized as shown in Scheme II. Carbaldehydes of Formula D can be reacted with 1,2-dihydroxylamines of Formula E to afford imidazolines of Formula F, which then are oxidized to the corresponding nitronyl-N-oxides by known procedures (e.g. Wu et al. Bioorganic & Medicinal Chemistry 14 (2006) 5711-5720):

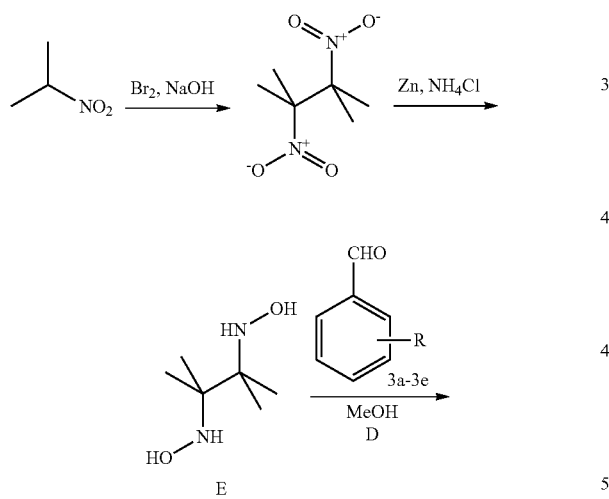

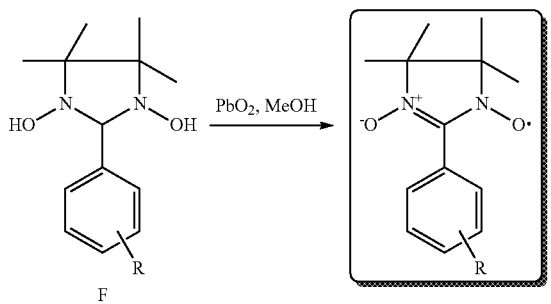

Example 2

III. Preparation of 2,3-Dimethyl-2,3Dinitrobutane

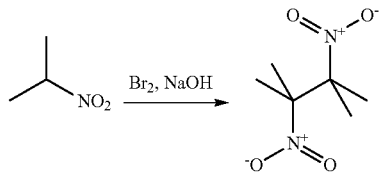

At −5° C., Br$_2$ (29 mL, 0.55 mol) were added dropwise to the solution of 2-nitropropane (100 g, 1.12 mol) in 188 mL (6.0 mol/L) of aqueous NaOH. Ethanol (371 mL) was added into the mixture during stirring. The reaction mixture was stirred at 84° C. for 3 h. The hot reaction mixture was transferred into 1160 mL of ice water. The formed colorless crystals were collected by filtration to yield the desired compound (82.56 g, 83%). $^1$HNMR (400 MHz, MeOD): δ 1.7 (s, 3H).

IV. Preparation of 2,3-Bis(Hydroxylamino)-2,3-Dimethylbutane

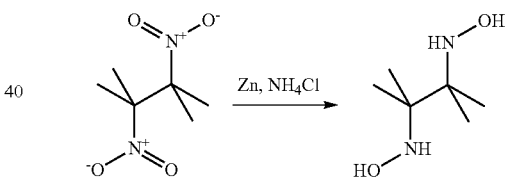

2,3-Dimethyl-2,3-dinitrobutane (82.56 g, 0.47 mmol) was dissolved in a mixture of THF (1407 mL) and water (235 mL). To this solution cooled to 8-10° C., Zn powder (126.9 g, 1.95 mol) was added in one portion. A solution of NH$_4$Cl (202.1 g, 3.77 mol) in H$_2$O (705 mL) was added dropwise to this slurry, with continued stirring for 1 h at 10° C., and the flask was stored in cooled water for 16 h. The slurry was filtered, and the precipitate was carefully washed with THF (4×200 mL). The precipitate was then dried by three washings with diethyl ether and collected. The solution was evaporated under vacuum until THF ceased to distill off. Then the solution was protected from air, and sodium carbonate (235 g) and sodium chloride (141 g) were added with cooling. Continuous extraction with chloroform (1880 mL) was performed over 18 h. The filtrate was concentrated to give oil product, then added petroleum ether to this mixture and stirred for 30 min at room temperature, filtered, dried, to afford a white powder (12.8 g, 18.4% yield). $^1$HNMR (400 MHz, DMSO): δ 6.89 (s, 1H), 5.34 (s, 1H), 0.96 (s, 3H).

Preparation of 1,3-Dihydroxy-2-(4-methoxyphenyl)-4,4,5,5-tetramethylimidazolidine

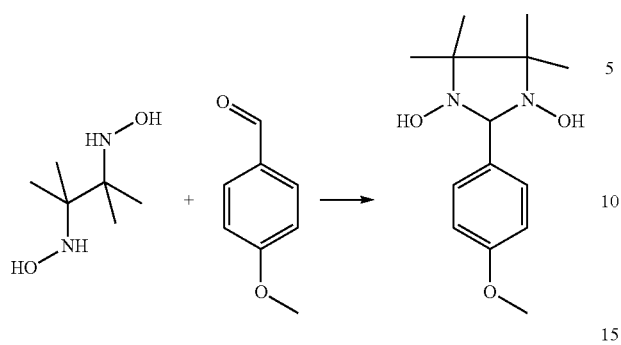

A solution of 2,3-bis(hydroxylamino)-2,3-dimethylbutane (1.3 g, 8.8 mmol) and 4-methoxy-benzaldehyde (1.2 g, 8.8 mmol) in methanol (10 mL) was stirred at room temperature until reactants disappeared as TLC indicated. 1,3-Dihydroxy-2-(4-methoxyphenyl)-4,4,5,5-tetramethylimidazolidine was obtained by filtration, the filtrate was evaporated under reduced pressure to obtain the second crop of the title compound. The combined compound was then washed with petroleum ether and used for the next reaction (0.8 g, 34% yield). $^1$HNMR (400 MHz, DMSO): δ 7.63 (s, 1H), 7.32 (d, 1H, J=6.8), 6.87 (d, 1H, J=5.8), 4.42 (s, 1H), 3.72 (s, 3H), 1.06 (s, 3H), 1.02 (s, 3H).

V. Preparation of the Nitronyl N-Oxide

At room temperature the suspension of 0.8 g (3.0 mmol) of 1,3-dihydroxy-2-(4-methoxy-phenyl)-4,4,5,5-tetramethylimidazolidine and 2.1 g of lead dioxide in 30 mL methanol was stirred until the reaction mixture turn blue. After filtration, the filtrate was evaporated under reduced pressure, and purified by column chromatography. The combined fraction was concentrated and crystallized on addition of little petroleum ether at −78° C. The dark blue crystalline product after washing with little cold petroleum ether, weighed 0.7 g (88%).

Methods

Provided herein are methods of paper or pulp treatment and/or paper deinking. For example, some methods pulp or paper processes to, e.g., depolymerize lignin, and, prevent discoloration of paper, pulp caused by lignins. Treatment of paper, pulp, and lignin-containing compositions is described, for example, in U.S. Pat. Nos. 5,179,021, 5,116,746, 5,407,827, 5,405,769, 5,395,765, 5,369,024, 5,457,045, 5,434,071, 5,498,534, 5,591,304, 5,645,686, 5,725,732, 5,759,840, 5,834,301, 5,871,730 6,057,438, 5,486,468 and 5,770,012.

In some embodiments, a composition comprising lignin (e.g., wood pulp) is contacted with at least one compound of Formula I or Formula II under conditions wherein the lignin is depolymerized, softened, or liquified. Preferably, the paper, pulp, or lignin-containing composition is contacted with one of the following compounds, or any combination thereof:

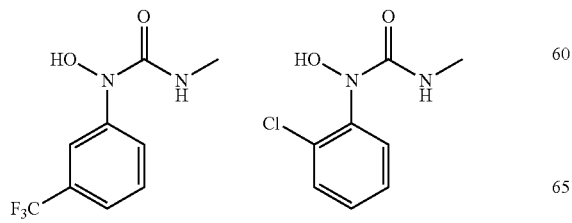

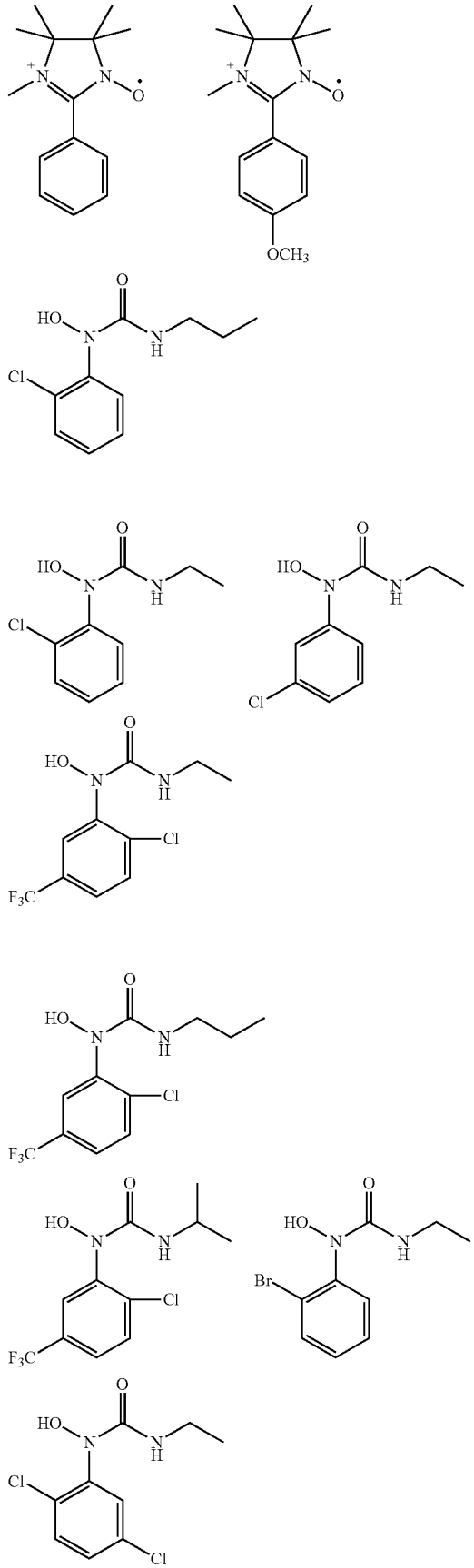

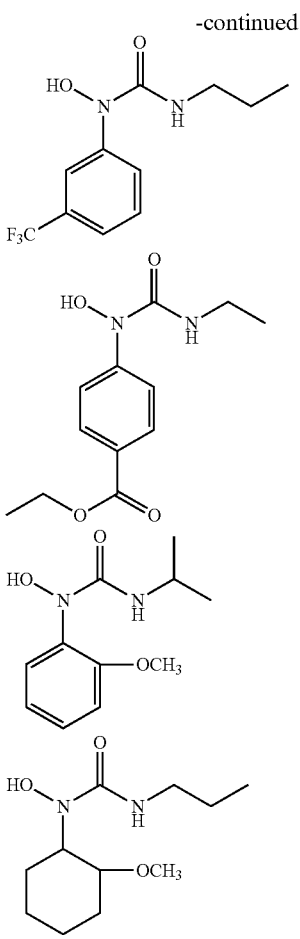

The final concentration of the compound (e.g., compound of Formula I or Formula II) can be readily determined by the skilled artisan. In some embodiments, the compound of Formula I or II is provided at a final concentration of 1 µM, 5 µM, 10 µM, 50 µM, 100 µM, 300 µM, 500 µM, 1 mM, 5 mM, 10 mM, 50 mM, 100 mM, 300 mM, 500 mM, 1 M, 2 M, 5 M or above, or any number in between.

In some embodiments, the paper, wood pulp or lignin containing composition can also be contacted with a mediator selected from one or more of the following: violuric acid; 2,6,6-tetrarmethylpiperidein-1-yloxy (TEMPO); 1-hydroxybenzotriazole (HBT); 2,2'-azino-bis(3-ethylbenzthiazoline-6-sulfonic acid) (ABTS); syringaldazine; N-benzoyl-N-phenyl hydroxylamine (BPHA); N-hydroxyphthalimide, 3-Hydroxy-1,2,3-benzotriazin-4-one; promazine; 1,8-Dihydroxy-4,5-dinitroanthraquinone; phenoxazine; anthraquinone; 2-hydroxy-1,4-naphthoquinone; phenothiazine; anthrone; anthracene, anthrarufin, anthrarobin, dimethoxyphenol (DMP); ferulic acid; catechin; epicatechin; homovanillic acid (HMV); and 2,3-dihydroxybenzoic acid (2,3-DHB); or any combination thereof.

Preferably, the paper, pulp, or lignin containing composition is treated under alkaline conditions, such as pH 7.25, 7.5, 8, 8.25, 8.5, 8.75, 9.0, 9.25, 9.5, 9.75, 10.0, 10.25, 10.5, 10.75, 11, or above.

In some embodiments, the paper, pulp or lignin-containing composition is treated at temperatures above 22° C., e.g., 25° C., 30° C., 35° C., 40° C., 45° C., 50° C., 55° C., 60° C., 65° C., 70° C., 80° C., 85° C., 90° C., 95° C., or above, or any number in between. In preferred embodiments, the pulp, paper or lignin containing composition is treated at temperatures above 60° C., such as 65° C. to 70° C. or above. Accordingly, in some embodiments, the paper, pulp, or lignin containing composition is treated between 65° C. and 75° C. at a pH of 8 or above, such as pH 9, 9.5 or 10 or more.

In some embodiments, the paper, pulp, or lignin-containing composition is also contacted with a laccase. For example, in some embodiments, the paper, pulp, or lignin-containing composition is contacted with a laccase polypeptide described herein, such as a polypeptide of SEQ ID NO: 2, SEQ ID NO: 4, or variants thereof. It will be appreciated, however, that laccases now known (See, e.g., U.S. Pat. No. 5,480,801 and U.S. patent application Ser. No. 10/567,536), or discovered in the future are useful in the embodiments described herein. Preferably, the laccase is a thermostable alkaline laccase.

In some embodiments, the treatment of paper, pulp, or lignin-containing composition can also include the use of any combination of other enzymes such as catalases, cellulases, endoglycosidases, endo-beta-1,4-laccases, amyloglucosidases, glucose isomerases, glycosyltransferases, lipases, phospholipases, lipooxygenases, beta-laccases, endo-beta-1,3(4)-laccases, cutinases, peroxidases, amylases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

Other embodiments provide methods of oxidizing, breaking up or disrupting a lignin-containing composition by contacting the lignin-containing composition with one or more of the laccase polypeptides disclosed herein. For example, in some embodiments, the lignin-containing composition can be contacted with a polypeptide that comprises, consists essentially of, or consists of the polypeptide of SEQ ID NO: 2 or SEQ ID NO: 4, or any variant thereof.

In some embodiments, the composition comprising lignin (e.g., wood pulp) is also contacted with at least one compound of Formula I or Formula II under conditions wherein the lignin is depolymerized, softened, or liquified. Preferably, the paper, pulp, or lignin-containing composition is contacted with one of the following compounds, or any combination thereof:

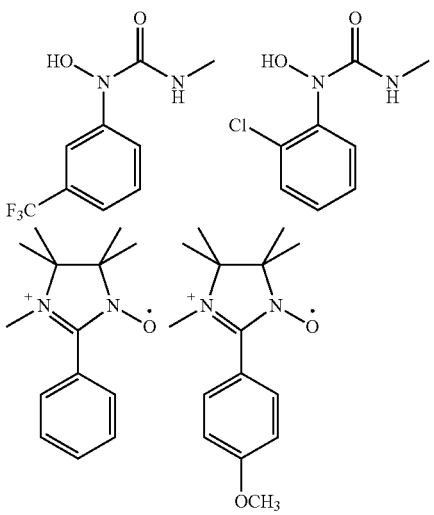

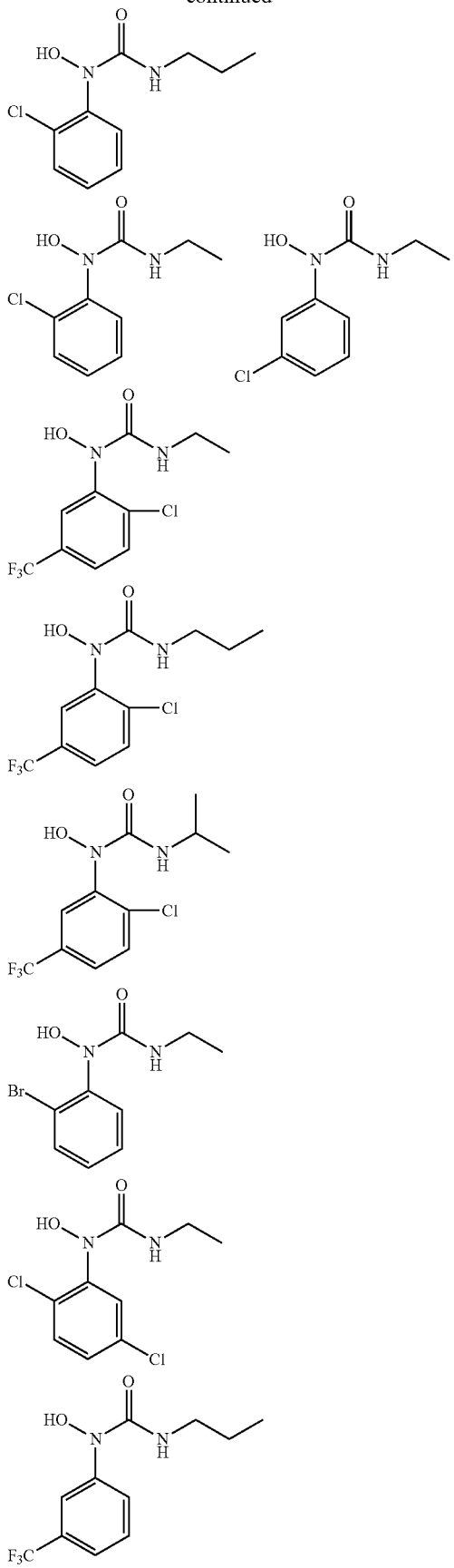
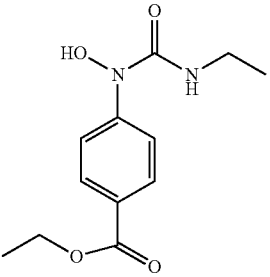
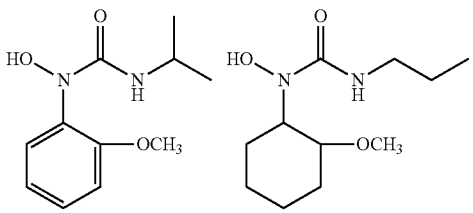

In some embodiments, the paper, wood pulp or lignin-containing composition can also be contacted with a mediator selected from one or more of the following: violuric acid; 2,6,6-tetrarmethylpiperidein-1-yloxy (TEMPO); 1-hydroxy-benzotriazole (HBT); 2,2'-azino-bis(3-ethylbenzthiazoline-6-sulfonic acid) (ABTS); syringaldazine; N-benzoyl-N-phenyl hydroxylamine (BPHA); N-hydroxyphthalimide, 3-Hydroxy-1,2,3-benzotriazin-4-one; promazine; 1,8-Dihydroxy-4,5-dinitroanthraquinone; phenoxazine; anthraquinone; 2-hydroxy-1,4-naphthoquinone; phenothiazine; anthrone; anthracene, anthrarufin, anthrarobin, dimethoxyphenol (DMP); ferulic acid; catechin; epicatechin; homovanillic acid (HMV); and 2,3-dihydroxybenzoic acid (2,3-DHB); or any combination thereof.

Preferably, the paper, pulp, or lignin-containing composition is treated under alkaline conditions, such as pH 7.25, 7.5, 8, 8.25, 8.5, 8.75, 9.0, 9.25, 9.5, 9.75, 10.0, 10.25, 10.5, 10.75, 11, or above.

In some embodiments, the paper, pulp or lignin-containing composition is treated at temperatures above 22° C., e.g., about 25° C., 30° C., 35° C., 40° C., 45° C., 50° C., 55° C., 60° C., 65° C., 70° C., 80° C., 85° C., 90° C., 95° C., or above, or any number in between. In preferred embodiments, the pulp, paper or lignin-containing composition is treated at temperatures above 60° C., such as 65° C. to 70° C. or above. Accordingly, in some embodiments, the paper, pulp, or lignin-containing composition is treated between 65° C. and 75° C. at a pH of 8 or above, such as pH 9, 9.5 or 10 or more.

For example, in some embodiments, the lignin-comprising compound is contacted with the polypeptide of SEQ ID NO: 4, or variant thereof, and (Mediator 71)

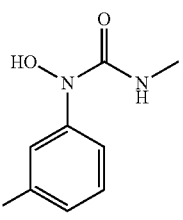

under alkaline conditions, for example pH 8 or above. In some embodiments, the treatment proceeds between 55° C.-70° C.

Other embodiments relate to methods of oxidizing a phenolic or aromatic substrate. The phenolic substrate can be contacted with a compound of Formula I or II. In preferred embodiments, the one or more of the following: violuric acid; 2,6,6-tetrarmethylpiperidein-1-yloxy (TEMPO); 1-hydroxybenzotriazole (HBT); 2,2'-azino-bis (3-ethylbenzthiazoline-6-sulfonic acid) (ABTS); syringaldazine; N-benzoyl-N-phenyl hydroxylamine (BPHA); N-hydroxyphthalimide, 3-Hydroxy-1,2,3-benzotriazin-4-one; promazine; 1,8-Dihydroxy-4,5-dinitroanthraquinone; phenoxazine; anthraquinone; 2-hydroxy-1,4-naphthoquinone; phenothiazine; anthrone; anthracene; anthrarufin; anthrarobin; dimethoxyphenol (DMP); ferulic acid; catechin; epicatechin; homovanillic acid (HMV); and 2,3-dihydroxybenzoic acid (2,3-DHB); or any combination thereof.

Preferably, the pheonlic substrate is treated under alkaline conditions, such as pH 7.25, 7.5, 8, 8.25, 8.5, 8.75, 9.0, 9.25, 9.5, 9.75, 10.0, 10.25, 10.5, 10.75, 11, or above.

In some embodiments, the phenolic substrate is treated at temperatures above 22° C., e.g., 25° C., 30° C., 35° C., 40° C., 45° C., 50° C., 55° C., 60° C., 65° C., 70° C., 80° C., 85° C., 90° C., 95° C., or above, or any number in between. In preferred embodiments, the phenolic substrate is treated at temperatures above 60° C., such as 65° C. to 70° C. or above. Accordingly, in some embodiments, the phenolic substrate is treated between 65° C. and 75° C. at a pH of 8 or above, such as pH 9, 9.5 or 10 or more.

Also provided herein are methods for oxidizing a fiber-containing composition. For example, in some embodiments, the fiber-containing composition can be contacted with a polypeptide that comprises, consists essentially of, or consists of the polypeptide of SEQ ID NO: 2 or SEQ ID NO: 4, or any variant thereof.

In some embodiments, the composition comprising fiber is also contacted with at least one compound of Formula I or Formula II. Preferably, the fiber-containing composition is contacted with one of the following compounds, or any combination thereof:

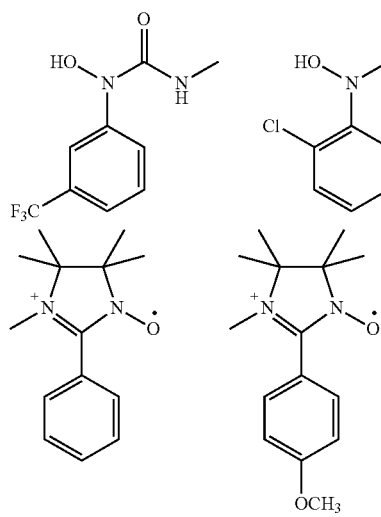

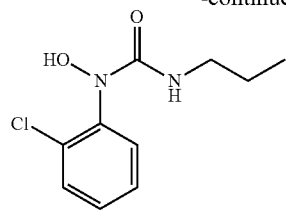

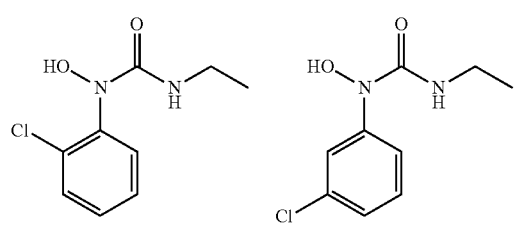

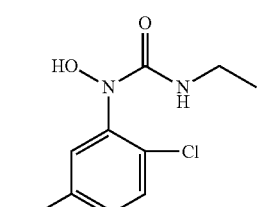

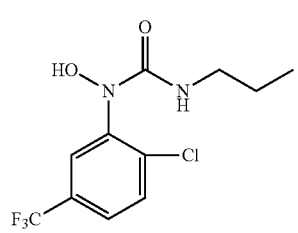

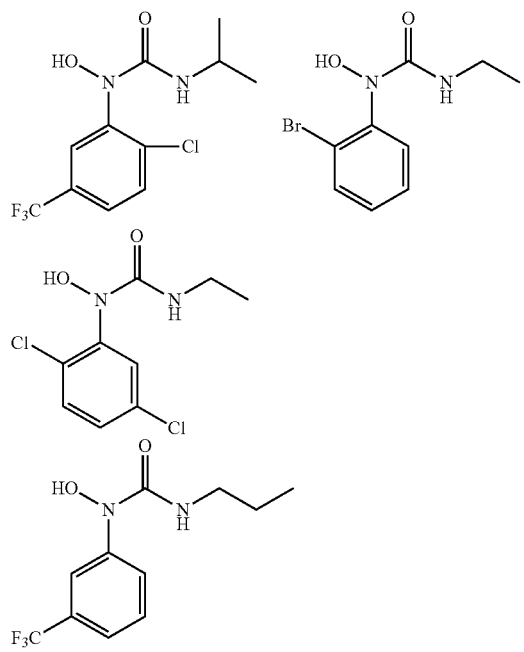

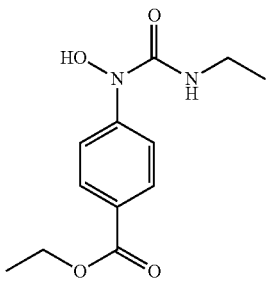

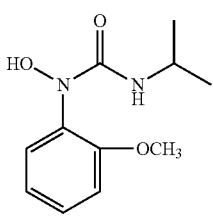

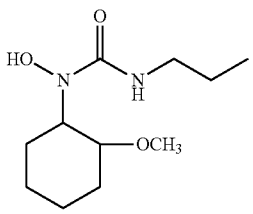

In some embodiments, the fiber-containing composition can also be contacted with a mediator selected from one or more of the following: violuric acid; 2,6,6-tetrarmethylpiperidein-1-yloxy (TEMPO); 1-hydroxybenzotriazole (HBT); 2,2'-azino-bis(3-ethylbenzthiazoline-6-sulfonic acid) (ABTS); syringaldazine; N-benzoyl-N-phenyl hydroxylamine (BPHA); N-hydroxyphthalimide, 3-Hydroxy-1,2,3-benzotriazin-4-one; promazine; 1,8-Dihydroxy-4,5-dinitroanthraquinone; phenoxazine; anthraquinone; 2-hydroxy-1,4-naphthoquinone; phenothiazine; anthrone; anthracene, anthrarufin, anthrarobin, dimethoxyphenol (DMP); ferulic acid; catechin; epicatechin; homovanillic acid (HMV); and 2,3-dihydroxybenzoic acid (2,3-DHB); or any combination thereof.

Preferably, fiber-containing composition is treated under alkaline conditions, such as pH 7.25, 7.5, 8, 8.25, 8.5, 8.75, 9.0, 9.25, 9.5, 9.75, 10.0, 10.25, 10.5, 10.75, 11, or above.

In some embodiments, fiber-containing composition is treated at temperatures above 22° C., e.g., 25° C., 30° C., 35° C., 40° C., 45° C., 50° C., 55° C., 60° C., 65° C., 70° C., 80° C., 85° C., 90° C., 95° C., or above, or any number in between. In preferred embodiments, the fiber-containing composition is treated at temperatures above 60° C., such as 65° C. to 70° C. or above. Accordingly, in some embodiments, the paper, pulp, or lignin containing composition is treated between 65° C. and 75° C. at a pH of 8 or above, such as pH 9, 9.5 or 10 or more.

For example, in some embodiments, the fiber-comprising compound is contacted with the polypeptide of SEQ ID NO: 4, or variant thereof, and

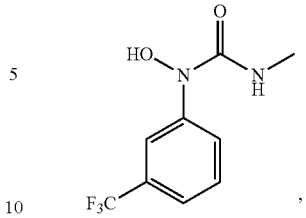

(Mediator 71)

under alkaline conditions, for example pH 8 or above. In some embodiments, the treatment proceeds between 55° C.-70° C.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Having now generally described the invention, the same will become better understood by reference to certain specific examples which are included herein for purposes of illustration only and are not intended to be limiting unless other wise specified. All referenced publications and patents are incorporated, in their entirety by reference herein.

Example 1: Isolation of Fungal Laccase Genes

The following example describes the isolation of fungal laccase genes. A collection of fungal strains was obtained from a high pH environment (pH≥0.8). A phylogenetic tree was constructed using publicly available nucleic acid sequences, as well as genomic sequences determined from the collection of fungal strains. The phylogenetic tree of SWISSPROT™ Pfam HMM Cu-oxidase sequences and gene predictions from fungal genomes shows five major clades: laccases from Viridiplantae, various functions from various sources, laccases from Ascomycetes, laccases from Arthropoda, and laccases from Basidiomycetes.

Sequence alignments were used to identify conserved sequences from Ascomycete and Basidiomycete sub-clades, which includes *Cochiobolus heterostrophus, Fusarium verticillioides*, and *Botrytis cinerea* 1. Degenerate primers designed based on the conserved sequences, to amplify DNA fragments in the range of 0.5-1 kilobase (kb). Chromosomal DNA was isolated from fungal strains using routine protocols, and used as a template in PCR reactions with the degenerate primers.

PCR products in the size range of 0.5-1 kilobase (kb) were cloned and sequenced to confirm amplification of laccase gene fragments. DNA fragments confirmed to be laccase genes were extended by several additional PCR amplifications using routine molecular biology techniques to obtain full-length genes. Sequence analysis was performed to determine putative full-length laccase genes, start/stop codons, and intron/exon junctions. A total of 36 full-length laccase genes were discovered form Ascomycete isolates and 5 full-length laccase genes from Basidiomycete isolates.

Sequences were aligned using the BLAST algorithm against the non-redundant NCBI database. High-scoring pairs (HSPs) corresponded approximately to exons that aligned well with publicly known laccase sequences, and were manually extended or truncated up to the correct exon/intron boundaries. Missing exons at the 5' end of the gene were searched for by visual inspection of the 3-frame translations of the clone sequence to identify the most likely start codon.

Putative laccase genes from *Cochliobolus, Fusarium*, and *Botrytis* located in the Ascomycete clade were targeted for further analysis.

Example 2: Laccase Subcloning and Expression

The coding sequences for the candidate laccases determined above were cloned into an expression vector that is capable of integrating into the *Aspergillus niger* genome through homologous recombination, such that the coding sequences were operably linked to a glucoamylase promoter. Following PEG-mediated protoplast transformation, transformants containing the expression cassette were selected using a selectable marker also present on the vector. The native signal peptide sequences from the laccase genes were included in the construct.

After sequence verification, the constructs were used to transform *Aspergillus niger*, selecting on Selective Regeneration Medium for the utilization of acetamide as sole nitrogen-source. Six transformants from each candidate were streaked onto Selective Medium for single colonies and grown for five days at 30° C. A single colony from each strain was then streaked onto Potato Dextrose Agar (PDA) for single colonies, after which one colony was selected and streaked for confluent growth on PDA (including 0.5 mM $CuSO_4$ in the PDA used for sporulation). A spore suspension was recovered for each transformant and used to inoculate CSL-Seclin starter cultures. After overnight growth, the starter cultures were used to inoculate CSM/MES in baffled flasks. The CSM/MES cultures were grown at 30° C. for five days.

To verify that the *Aspergillus* transformants expressed and secreted a protein with laccase activity, samples of culture supernatant were analyzed for the ability to oxidize 2, 2'-azino-bis(3-ethylbenzthiazoline-6sulfoninc acid (ABTS) at pH 5.2. Briefly, a 1 mL sample of the culture was centrifuged at 5,000 rpm for 5 minutes. 20 μL of the culture supernatant was added to 180 μL of 1 mM ABTS in 50 mM sodium acetate pH 5.2 in 96-well microtiter plate. Laccase activity is measured by following $\Delta A420$ nm/min with spectrophotometer. One ABTS unit is the amount of laccase resulting in 1 absorbance unit change in one minute. Transformants that provided the highest yield of laccase in the supernatant were used for further testing.

Example 3: Determination of pH Optimum on Syringaldazine by Candidate Laccases

To determine the pH optimum of the laccases expressed in *Aspergillus*, the laccases were assayed for their activity on a low redox mediator syringaldazine (SGZ) over a pH range from 4-11 at room temperature. Initial rates for each laccase on SGZ were measured at room temperature at pH range from 4-11. SGZ oxidation was determined in Britten-Robinson buffer, pH 5.0 to 11.0, with 10% ethanol (coming from SGZ stock solution) by monitoring the absorbance change at 530 nm with an extinction coefficient of 65 $mM^1$ $cm^{-1}$ (Bauer and Rupe, 1971, Analytical Chemistry 43: 421-425) at room temperature. Laccase activity using SGZ as a substrate was assayed by mixing 800 μl of assay buffer (40 μM $CuSO_4$–25 mM sodium acetate pH 5.5) with 20 μl of culture supernatant isolated as described in Example 2, and 60 μl of 0.28 mM syringaldazine in 50% ethanol. The absorbance at 530 nm was measured over time in a UV-VIS spectrophotometer.

More than thirty laccases were tested. The majority of the candidate laccases tested showed highest activity in acidic range ($pH_{opt}$ 4-6). However, two laccases (BD22449 from *Cochiobolus heterostrophus* and BD22865 from *Fusarium verticillioides*) exhibited a $pH_{opt}$>8 on SGZ. The two laccases were analyzed further.

Example 4: TEMPO, Violuric Acid and HBT Oxidation by Candidate Laccases

Laccases that exhibited a $pH_{opt} \geq 8$ on SGZ as described in Example 3 were further characterized by assaying their ability to oxidize 2, 2, 6, 6-tetrarmethylpiperidein-1-yloxy (TEMPO) at pH 8 at room temperature. Briefly, 50 μL of test culture supernatants isolated as described in Example 2 was incubated with 950 uL TEMPO (1 mM in Britton-Robinson Buffer at pH 8) at 22° C. in an OXYTHERM™ oxygen measurement instrument (Hansatech, England). Oxygen consumption was measured over time according to the manufacturer's instructions.

BD22449 (SEQ ID NO: 2) did not show TEMPO oxidation at pH 8 at room temperature. BD22865 (SEQ ID NO: 4) showed TEMPO oxidation with oxygen consumption rate of 250 nmol/min/mg. The ability of BD22865 (SEQ ID NO: 4) to oxidize mediators with higher redox potentials such as violuric acid and 1-hydroxybenzotriazole (HBT) at pH 8 at room temperature was also tested. Briefly, 50 μL of BD22865 culture supernatant isolated as described in Example 2 was incubated with 950 μL violuric acid (1 mM in Britton-Robinson Buffer at pH 8) or HBT (1 mM in Britton-Robinson Buffer) at pH 8 at 22° C. in an OXY-THERM™ oxygen measurement instrument. Oxygen consumption was measured as described above. SEQ ID NO:4 (BD22865) was able to oxidize both violuric acid and HBT with oxygen consumption rates of 150 nmol/min/mg and 100 nmol/min/mg, respectively under the conditions described herein. These results indicate that BD22865 is a high redox potential laccase and BD22449 is a medium redox potential.

Figure 2:
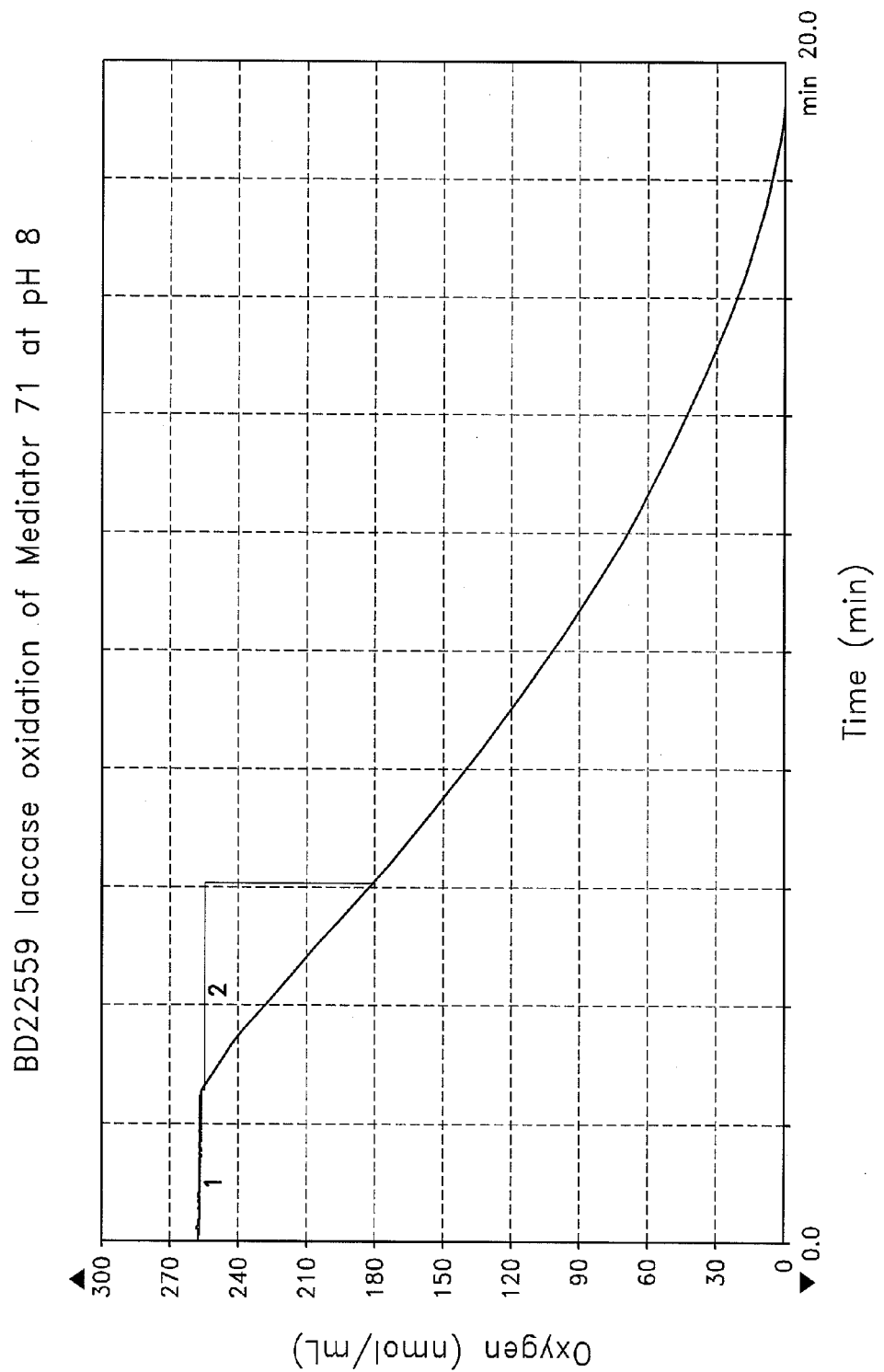
FIG. 2 is a graph showing the consumption of oxygen (nmol/mL) over time, indicative of oxidation of Mediator 71 at pH 8 by the BD22449 laccase measured as described in Example 5.
Figure 3:
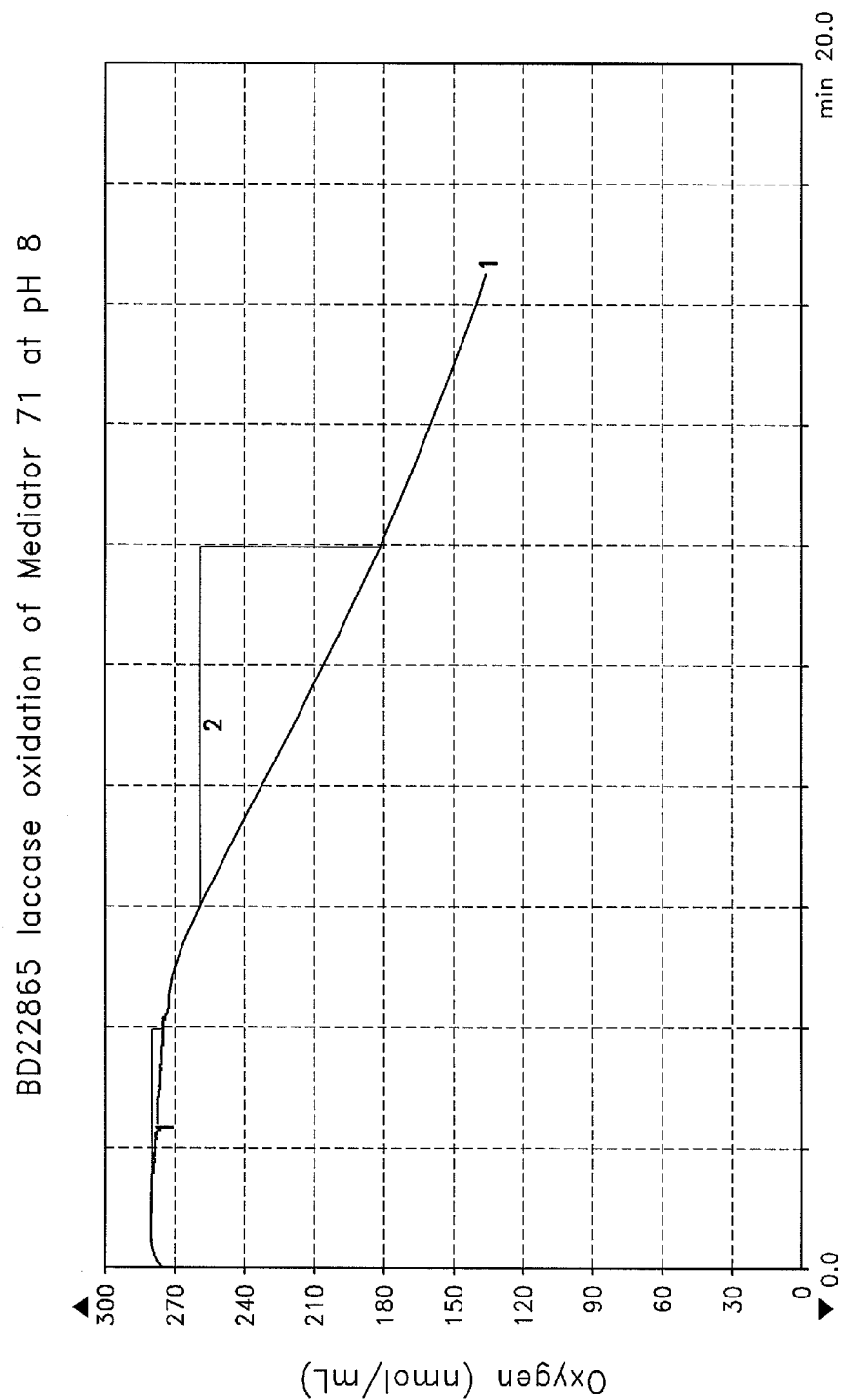
FIG. 3 is a graph showing the consumption of oxygen (nmol/mL) over time, indicative of oxidation of Mediator 71 at pH 8 by the BD22865 laccase measured as described in Example 5.

Example 5: Oxidation of Mediators Capable of Oxidizing Lignin (3-(3'-Trifluoromethylphenyl)-3-hydroxy-1-methylurea), "Mediator 71" is capable of delignifying pulp. Mediator 71 was identified as the most efficient Mediator 71t pH 5 and pH 8. BD22449 (SEQ ID NO:2), BD22865 (SEQ ID NO:4) and *Trametes versicolor* laccase (used as a control) were assayed for their ability to oxidize Mediator 71 at pH 8 using oxygen electrode. Briefly, 50 µL of BD22449 or BD22865 culture supernatant isolated as described in Example 2 was incubated with 950 µL Mediator 71 dissolved in Britton-Robinson Buffer to a final concentration of 1 mM at pH 8. The consumption of oxygen was measured at room temperature in an OXYTHERM™ oxygen measurement instrument over time as described above. The results of the experiments are shown in FIGS. 1, 2, and 3. *Trametes* laccase did not oxidize Mediator 71 at pH 8, whereas BD22449 and BD22865 laccases had specific activities of 677 nmol/min/mg and 1350 nmol/min/mg, respectively (specific activities for laccase preparation, not for purified protein).

Figure 4:
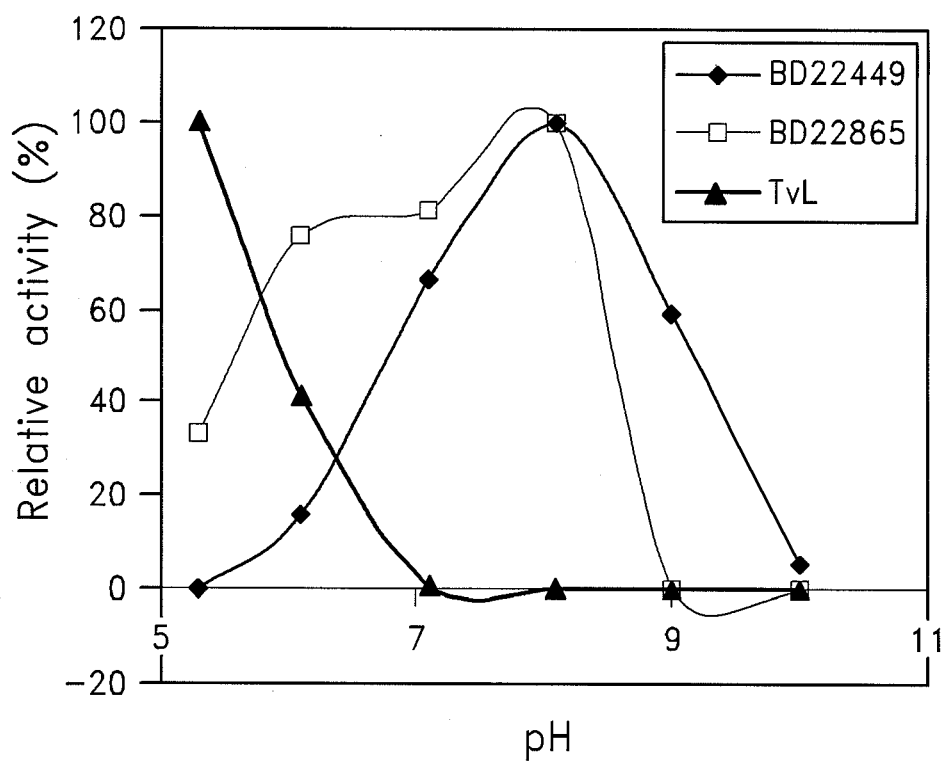
FIG. 4 is a graph showing the relative activity of *Trametes versicolor* (triangles), BD22449 (diamonds), and BD22865 (squares) on Mediator 71 at the indicated pH's, at room temperature, measured as described in Example 5.

Next, the $pH_{opt}$ for the catalysis of the oxidation of Mediator 71 was determined for each laccase. 50 L of BD22449 or BD22865 culture supernatant isolated as described in Example 2 was incubated with 950 L Mediator 71 dissolved in Britton-Robinson Buffer to a final concentration of 1 mM at pH 5, 6, 7, 8, 9, or 10. The consumption of oxygen over 20 min at room temperature was determined in an OXYTHERM™ oxygen measurement instrument over time as described above. The results are presented in FIG. 4. Both BD22865 and BD22849 exhibited optimum oxidation of Mediator 71 at pH 8. By contrast, the *Trametes* laccase had no activity on Mediator 71 at pH 7 or above.

Example 6: Thermotolerance of Fungal Laccases

Laccases BD22449 and BD22865, identified and characterized in Examples 1-5 above were assayed for thermotolerance. Briefly, each laccases was tested at 50° C., 60° C. and 70° C. for 0-60 minutes wherein the residual activity on ABTS was measured. Supernatants from the *Aspergillus* cultures expressing BD22449 (SEQ ID NO:2) and BD22865 (SEQ ID NO:4) were isolated as described in Example 2. Supernatants were incubated at 50° C., 60° C. or 70° C. for 1 min, 5 min, 10 min, 30 min, and 60 min. For each time point, the oxidation of 2, 2'-azino-bis(3-ethylbenzthiazoline-6-sulfonic acid) (ABTS) by the laccase was measured using an OXYTHERM™ oxygen measurement instrument.

Figure 5:
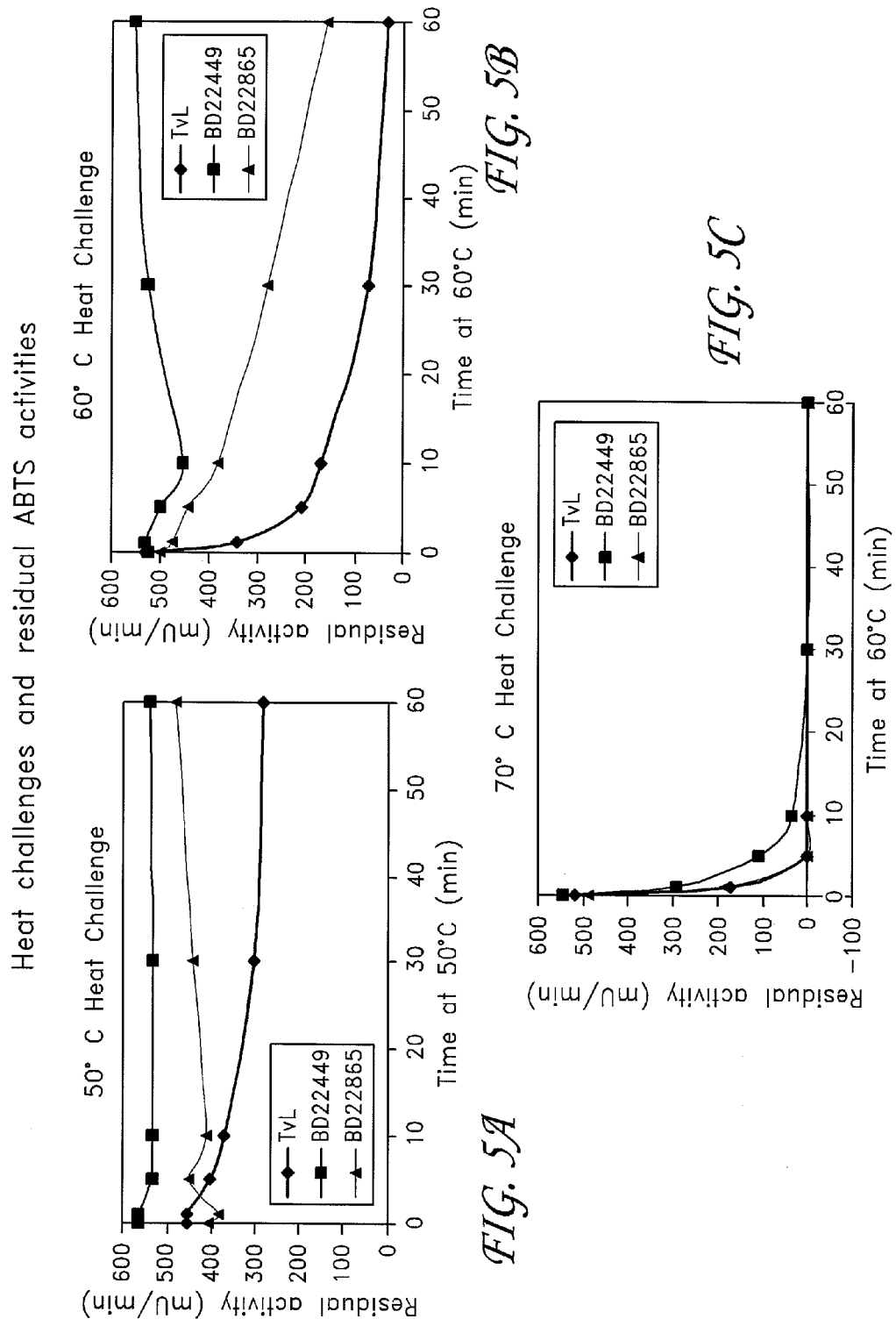
FIGS. 5A-5C are graphs showing the residual activity of *Trametes versicolor* (triangles), BD22449 (diamonds), and BD22865 (squares) on 1-hydroxybenzotriazole (HBT); 2,2'-azino-bis(3-ethylbenzthiazoline-6-sulfonic acid) (ABTS) following treatment for the indicated times at 50° C.

The results are shown in FIGS. 5A-C. Both BD22449 (SEQ ID NO:X) and BD22865 (SEQ ID NO:X) laccases tolerated a 50° C. heat challenge well for an hour, but *Trametes* laccase was somewhat challenged (data not shown). At 60° C., BD22449 was unchallenged for an hour. BD22865 had a half-life at 60° C. of ~40 min and *Trametes* laccase of <5 min. A 70° C. challenge quickly denatured all three laccases.

BD22449 remained approximately 100% active after an hour at 60° C., which is likely to be the highest temperature a laccase would be exposed to in the D(0) stage (most likely point of laccase application). BD22865 remained about 40% active after an hour at 60° C.; however it had about twice the specific activity on Mediator 71 compared to BD22449.

Example 7: Kinetics of Fungal Laccase Activity

Figure 6:
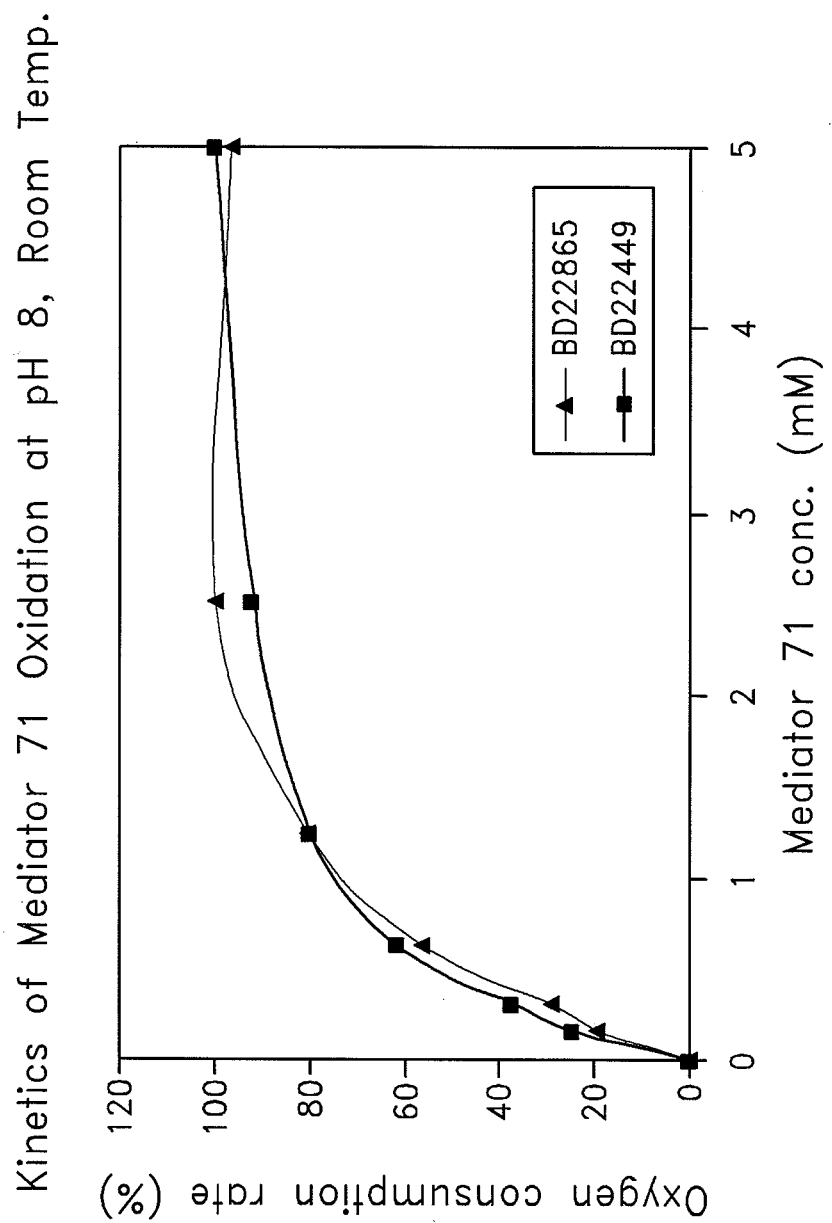
FIG. 6 shows the kinetics of the oxidation of Mediator 71 by BD22449 laccase (squares) and by BD22865 laccase at pH 8, room temperature, measured as described in Example 7.

The kinetics of the catalysis of oxidation of Mediator 71 by the fungal laccases described above was determined. Using the OXYTHERM™ oxygen measurement instrument, oxygen consumption rates at pH 8 at room temperature by BD22449 (SEQ ID NO:2) and BD22865 (SEQ ID NO:4) were measured in different mediator concentrations. The results are shown in FIG. 6.

Both laccases obeyed Michaelis-Menten (or saturation) kinetics. Both laccases showed similar saturation kinetics with respect to Mediator 71 concentration: KM on Mediator 71 was ~500 µM for both laccases. The maximal rate was obtained at mediator concentrations exceeding ~2.5 mM and KM was around 500 µM for both lead laccases. KM for oxygen was not measured, but at mediator concentrations exceeding 1 mM, both laccases efficiently consumed all the oxygen in the oxygen electrode reaction chamber. This indicates submicromolar KM on oxygen for both laccases, since 4 mediator molecules are oxidized per molecule of oxygen, and the starting oxygen concentration in the reaction chamber was ~250 µM.

Example 8: Delignification of Wood Pulp with Laccase and Mediator

Laccases BD22449 and BD22865, identified and characterized in Examples 1-5 above were assayed for wood pulp delignification with Mediator 71. Briefly, 1 gram of softwood pulp was treated with 3 mL of BD22449 or BD22865 culture supernatant isolated as described in Example 2 with 50 mg of Mediator 71 at 5% consistency in borate buffer pH 8 at 22° C. Laccase/mediator treatment was followed by extraction stage with 2.5% NaOH, 2% $H_2O_2$ at 75° C. Handsheets were made out of the treated pulp and brightness increase due to the laccase/mediator treatment was measured using Brightmeter Micro S-5 (Technidyne Corp. New Albany, Ind., USA). Brightness increase obtained with BD22449 and BD22865 with Mediator 71 was ~30% (data not shown).

Example 9: Oxidation of C6 in Glucopyranoside with Laccase and Mediator

Laccase BD22865, identified and characterized in Examples 1-5 above, is tested for oxidation glucopyranoside with the mediator TEMPO. 14.25 ABTS units of BD22865 is incubated in 12 mM TEMPO, 1 mg/mL glucopyranoside in 50 mM Borate buffer pH 8 for 16 hours at 22° C. The reaction mixture is diluted 1:100 and subjected to liquid chromatography and mass spectrometry on an Agilent C18 column using $H_2O$:acetonitrile (60:40) as running phase at 1 mL/min rate. Formation of oxidized glucopyranoside due to the laccase/TEMPO treatment is detected by identifying the carboxylate form in LCMS/MS spectra.

What is claimed is:

1. An isolated polynucleotide, comprising: a nucleic acid sequence comprising 80%-99% sequence identity with the nucleic acid sequence of SEQ ID NO: 1, wherein said polynucleotide encodes a polypeptide comprising laccase activity, oxidizes lignin under conditions of pH greater than or equal to pH 8.0, and retains laccase activity for at least about 5 minutes at greater than or equal to 60° C.

2. The isolated polynucleotide of claim 1, wherein said polynucleotide comprises a sequence that shares at least 90% sequence identity with SEQ ID NO: 1.

3. The isolated polynucleotide of claim 1, wherein said polynucleotide comprises a sequence that shares at least 95% sequence identity with SEQ ID NO: 1.

4. The isolated polynucleotide of claim 1, wherein said polynucleotide comprises a sequence that shares at least 97% sequence identity with SEQ ID NO: 1.

5. The isolated polynucleotide of claim 1, wherein said polynucleotide comprises a sequence that shares at least 99% sequence identity with SEQ ID NO: 1.

* * * * *